US009371311B2

(12) United States Patent
Mani et al.

(10) Patent No.: US 9,371,311 B2
(45) Date of Patent: *Jun. 21, 2016

(54) BENZOIMIDAZOL-2-YL PYRIMIDINE DERIVATIVES

(71) Applicant: Janssen Pharmaceutica NV, Beerse (BE)

(72) Inventors: Neelakandha S. Mani, San Diego, CA (US); Christopher L. Mapes, La Jolla, CA (US); Daniel J. Pippel, Del Mar, CA (US); Diego F. Broggini, Zurich (CH)

(73) Assignee: Janssen Pharmaceutica NV, Beerse (BE)

( * ) Notice: Subject to any disclaimer, the term of this patent is extended or adjusted under 35 U.S.C. 154(b) by 17 days.

This patent is subject to a terminal disclaimer.

(21) Appl. No.: 14/460,243

(22) Filed: Aug. 14, 2014

(65) Prior Publication Data

US 2014/0357865 A1 Dec. 4, 2014

Related U.S. Application Data

(60) Continuation-in-part of application No. 13/427,798, filed on Mar. 22, 2012, now Pat. No. 8,921,550, which is a division of application No. 12/459,224, filed on Jun. 29, 2009, now abandoned.

(60) Provisional application No. 61/076,759, filed on Jun. 30, 2008.

(51) Int. Cl.
*C07D 401/14* (2006.01)
*C07D 403/04* (2006.01)

(52) U.S. Cl.
CPC ............ *C07D 401/14* (2013.01); *C07D 403/04* (2013.01); *C07B 2200/13* (2013.01)

(58) Field of Classification Search
USPC ........................................................ 544/331
See application file for complete search history.

(56) References Cited

U.S. PATENT DOCUMENTS

| | | |
|---|---|---|
| 3,005,852 A | 10/1961 | Freyermuth |
| 3,609,152 A | 9/1971 | Hess |
| 3,931,195 A | 1/1976 | Dykstra |
| 4,190,601 A | 2/1980 | Decker |
| 4,191,828 A | 3/1980 | Horgan |
| 4,337,341 A | 6/1982 | Zimmerman |
| 5,614,524 A | 3/1997 | Matassa et al. |
| 5,621,097 A | 4/1997 | Brown |
| 5,880,140 A | 3/1999 | Anthony et al. |
| 5,883,105 A | 3/1999 | Anthony et al. |
| 5,939,439 A | 8/1999 | Anthony et al. |
| 5,945,422 A | 8/1999 | Doherty |
| 6,051,574 A | 4/2000 | Anthony et al. |
| 6,077,853 A | 6/2000 | Graham et al. |
| 6,210,394 B1 | 4/2001 | Demopulos et al. |
| 6,242,460 B1 | 6/2001 | Ettema |
| 6,372,743 B1 | 4/2002 | Darrow |
| 6,624,180 B2 | 9/2003 | South et al. |
| 6,693,194 B2 | 2/2004 | Jau |
| 6,803,362 B2 | 10/2004 | Carruthers |
| 6,828,338 B2 | 12/2004 | South et al. |
| 6,835,726 B2 | 12/2004 | Cushing et al. |
| 6,858,600 B2 | 2/2005 | Hamilton et al. |
| 6,916,938 B2 | 7/2005 | Oguma |
| 6,989,383 B1 | 1/2006 | Rosen et al. |
| 7,148,236 B2 | 12/2006 | Astles et al. |
| 7,250,427 B2 | 7/2007 | Breitenbucher et al. |
| 7,253,200 B2 | 8/2007 | Buzard |
| 7,312,246 B2 | 12/2007 | Hamilton et al. |
| 7,314,937 B2 | 1/2008 | Beavers et al. |
| 7,405,221 B2 | 7/2008 | Kopka et al. |
| 7,432,378 B2 | 10/2008 | Edwards |
| 7,507,737 B2 | 3/2009 | Edwards et al. |
| 7,576,092 B2 | 8/2009 | Chavez |
| 7,923,451 B2 | 4/2011 | Edwards et al. |
| 7,928,131 B2 | 4/2011 | Buzard et al. |
| 8,084,466 B2 | 12/2011 | Kindrachuk et al. |
| 8,309,720 B2 | 11/2012 | Cesco-Cancian |
| 8,343,989 B2 | 1/2013 | Edwards et al. |
| 8,598,189 B2 | 12/2013 | Edwards et al. |
| 8,835,633 B2 | 9/2014 | Cesco-Cancian et al. |
| 8,841,287 B2 | 9/2014 | Cai et al. |
| 8,859,575 B2 | 10/2014 | Conza et al. |
| 8,921,530 B2 | 12/2014 | Krarup |
| 2002/0077332 A1 | 6/2002 | Aronhime |
| 2003/0187026 A1 | 10/2003 | Li et al. |
| 2004/0048878 A1 | 3/2004 | Cai et al. |
| 2004/0058934 A1 | 3/2004 | Carruthers et al. |
| 2004/0105856 A1 | 6/2004 | Thurmond et al. |

(Continued)

FOREIGN PATENT DOCUMENTS

| | | |
|---|---|---|
| CN | 101032483 A | 9/2007 |
| JP | S59 42396 A | 3/1984 |

(Continued)

OTHER PUBLICATIONS

Bagshawe, K. et al, "Antibody-Directed Enzyme Prodrug Therapy: A Review", Drug Dev. Research, 1995, vol. 34, pp. 220-230.

Bertolini, G. et al, "A New Rational Hypothesis for the Pharmacophore of the Active Metabolite of Leflunomide, a Potent Immunosuppressive Drug" J. Med. Chem, 1997, vol. 40, pp. 2011-2016.

Bodor, N. et al, "Novel Approaches to the Design of Safer Drugs: Soft Drugs and Site-Specific Chemical Delivery Systems", Advances in Drug Research, 1984, vol. 13, pp. 224-331.

Fleisher, D. et al, "Improved oral drug delivery: solubility limitations overcome by the use of prodrugs", Advanced Drug Delivery Reviews, 1996, vol. 19, pp. 115-130.

Robinson, R. et al, "Discovery of the hemifumarate and (alpha-L-alanyloxy)methyl ether as prodrugs of an antirheumatic oxindole: prodrugs for the enolic OH group", J. Med. Chem, 1996, 39 (1), pp. 10-18.

(Continued)

*Primary Examiner* — James O Wilson
*Assistant Examiner* — Ebenezer O Sackey

(57) ABSTRACT

The present invention is directed to benzoimidazol-2-yl pyrimidine derivatives useful as histamine $H_4$ receptor modulators and processes for the preparation of such compounds.

1 Claim, 1 Drawing Sheet

(56) References Cited

U.S. PATENT DOCUMENTS

| | | |
|---|---|---|
| 2004/0127395 A1 | 7/2004 | Desai |
| 2004/0132715 A1 | 7/2004 | Dunford et al. |
| 2004/0224964 A1 | 11/2004 | O'Yang |
| 2004/0261190 A1 | 12/2004 | Eggenweiler |
| 2005/0070527 A1 | 3/2005 | Edwards et al. |
| 2005/0181023 A1 | 8/2005 | Young et al. |
| 2006/0089496 A1 | 4/2006 | Lam et al. |
| 2006/0281712 A1 | 12/2006 | Yen et al. |
| 2007/0043043 A1 | 2/2007 | Chen et al. |
| 2007/0099938 A1 | 5/2007 | Ohmoto et al. |
| 2007/0185163 A1 | 8/2007 | Hunt et al. |
| 2007/0238771 A1 | 10/2007 | Edwards et al. |
| 2007/0244126 A1 | 10/2007 | Edwards et al. |
| 2007/0265250 A1 | 11/2007 | Buzard et al. |
| 2008/0015200 A1 | 1/2008 | Chavez et al. |
| 2008/0119494 A1 | 5/2008 | Young et al. |
| 2008/0132513 A1 | 6/2008 | Che |
| 2008/0194577 A1 | 8/2008 | Cai et al. |
| 2008/0267887 A1 | 10/2008 | Yuan et al. |
| 2009/0137608 A1 | 5/2009 | Edwards et al. |
| 2009/0143302 A1 | 6/2009 | Yen et al. |
| 2009/0182142 A1 | 7/2009 | Furukubo et al. |
| 2010/0029942 A1 | 2/2010 | Cesco-Cancian |
| 2011/0076324 A1 | 3/2011 | Thurmond |
| 2011/0184016 A1 | 7/2011 | Lerner |
| 2013/0053561 A1 | 2/2013 | Cesco-Cancian |
| 2013/0202685 A1 | 8/2013 | Thurmond |
| 2013/0225816 A1 | 8/2013 | Cesco-Cancian |
| 2014/0038995 A1 | 2/2014 | Edwards |
| 2014/0066624 A1 | 3/2014 | Cesco-Cancian |
| 2014/0073795 A1 | 3/2014 | Cesco-Cancian |
| 2014/0121374 A1 | 5/2014 | Cesco-Cancian |
| 2014/0364607 A1 | 12/2014 | Conza et al. |

FOREIGN PATENT DOCUMENTS

| | | |
|---|---|---|
| JP | 61030576 A | 2/1986 |
| WO | WO 94/08577 | 4/1994 |
| WO | WO 97/36890 | 10/1997 |
| WO | WO 97/36898 | 10/1997 |
| WO | WO 98/31359 A1 | 7/1998 |
| WO | WO 98/44797 | 10/1998 |
| WO | WO 99/18079 A1 | 4/1999 |
| WO | WO 99/41253 | 8/1999 |
| WO | WO 99/65897 A1 | 12/1999 |
| WO | WO 00/78731 | 12/2000 |
| WO | WO 01/00610 A1 | 1/2001 |
| WO | WO 01/14376 | 3/2001 |
| WO | WO 01/47883 A1 | 5/2001 |
| WO | WO 01/58871 | 8/2001 |
| WO | WO 02/00647 A1 | 1/2002 |
| WO | WO 02/20495 A2 | 3/2002 |
| WO | WO 02/064096 | 8/2002 |
| WO | WO 02/072548 A2 | 9/2002 |
| WO | WO 02/076438 A2 | 10/2002 |
| WO | WO 02/078701 | 10/2002 |
| WO | WO 03/000254 A1 | 3/2003 |
| WO | WO 03/051366 A2 | 6/2003 |
| WO | WO 2004/012736 A1 | 2/2004 |
| WO | WO 2004/030625 A2 | 4/2004 |
| WO | WO 2004/050610 | 6/2004 |
| WO | WO 2004/110350 | 12/2004 |
| WO | WO 2005/014579 | 2/2005 |
| WO | WO 2005/032490 A2 | 4/2005 |
| WO | WO 2005/040135 | 4/2005 |
| WO | WO 2005/039485 A2 | 5/2005 |
| WO | WO 2005/044807 | 5/2005 |
| WO | WO 2005/092066 | 10/2005 |
| WO | WO 2005/115993 | 11/2005 |
| WO | WO 2006/025567 | 3/2006 |
| WO | WO 2006/063466 | 6/2006 |
| WO | WO 2006/102645 | 9/2006 |
| WO | WO 2006/138304 | 12/2006 |
| WO | WO 2007/003604 | 1/2007 |
| WO | WO 2007/044085 | 4/2007 |
| WO | WO 2007/059610 | 5/2007 |
| WO | WO 2007/070173 A2 | 6/2007 |
| WO | WO 2007/092095 | 8/2007 |
| WO | WO 2007/095753 | 8/2007 |
| WO | WO 2007/117399 | 10/2007 |
| WO | WO 2007/117400 | 10/2007 |
| WO | WO 2007/117401 | 10/2007 |
| WO | WO 2007/120690 A2 | 10/2007 |
| WO | WO 2007/124589 | 11/2007 |
| WO | WO 2007/134434 | 11/2007 |
| WO | WO 2008/060766 | 5/2008 |
| WO | WO 2009/068512 A1 | 6/2009 |
| WO | WO 2009/152287 | 12/2009 |
| WO | WO 2010/002774 A1 | 1/2010 |
| WO | WO 2010/002777 | 1/2010 |
| WO | WO 2012/060590 | 5/2012 |
| WO | WO 2012/069442 | 5/2012 |

OTHER PUBLICATIONS

Shan, D. et al, "Prodrug Strategies Based on Intramolecular Cyclization Reactions", Jour. Pharmaceutical Sciences, 1997, vol. 86(7), pp. 765-767.

Abarghaz, M. et al, "Regioselective Alkylation of the Exocyclic Nitrogen of Heterocyclic Amides via the Mitsunobu Reaction", Tetrahedron Letters, 1995, vol. 36, pp. 6463-6466.

Shultz, et al. "New Catalysts for the Oxidation of Sulfides to Sulfones with Hydrogen Peroxide" J. Org. Chem., 1963, 28, 1140.

Fung-Leung, W. P., et al. "Histamine H4 receptor antagonists: the new antihistamines?." Current opinion in investigational drugs (London, England: 2000) 5.11 (2004): 1174.

De Esch I.J.P., Thurmond R.L., Jongejan A., Leurs R., "The histamine H4 receptor as a new therapeutic target for inflammation", Trends in Pharmacological Sciences, (2005) 26 (9) , pp. 462-469.

Zhang, Mai, Robin L. Thurmond, and Paul J. Dunford. "The histamine H4 receptor: A novel modulator of inflammatory and immune disorders." Pharmacology & therapeutics 113.3 (2007): 594-606.

Thurmond, Robin L., Erwin W. Gelfand, and Paul J. Dunford. "The role of histamine H1 and H4 receptors in allergic inflammation: the search for new antihistamines." Nature Reviews Drug Discovery 7.1 (2008): 41-53.

Zhang, Mai, Jennifer D. Venable, and Robin L. Thurmond. "The histamine H4 receptor in autoimmune disease.", Expert Opinion (2006): 1443-1452.

Liu, et al., Cloning and Pharmacological Characterization of a Fourth Histamine Receptor ($H_4$) Expressed in Bone Marrow Mol Pharmacol Mar. 1, 2001 59:420-426; published online Mar. 1, 2001, doi:10.1124/mol.59.3.420.

Morse, Kelley L., et al. "Cloning and characterization of a novel human histamine receptor." Journal of Pharmacology and Experimental Therapeutics 296.3 (2001): 1058-1066.

Hofstra, Claudia L., et al. "Histamine H4 receptor mediates chemotaxis and calcium mobilization of mast cells." Journal of Pharmacology and Experimental Therapeutics 305.3 (2003): 1212-1221.

Lippert, Undine, et al. "Human skin mast cells express H2 and H4, but not H3 receptors." Journal of investigative dermatology 123.1 (2003): 116-123.

Voehringer, David, Kanade Shinkai, and Richard M. Locksley. "Type 2 immunity reflects orchestrated recruitment of cells committed to IL-4 production." Immunity 20.3 (2004): 267-277.

Gantner, Florian, et al. "Histamine H4 and H2 receptors control histamine-induced interleukin-16 release from human CD8+ T cells." Journal of Pharmacology and Experimental Therapeutics 303.1 (2002): 300-307.

Ikawa, Yoshiko, et al. "Histamine H4 receptor expression in human synovial cells obtained from patients suffering from rheumatoid arthritis." Biological and Pharmaceutical Bulletin 28.10 (2005): 2016-2018.

Jókúti, Adrienn, et al. "Histamine H4 receptor expression is elevated in human nasal polyp tissue." Cell biology international 31.11 (2007): 1367-1370.

(56) References Cited

OTHER PUBLICATIONS

Ling, Ping, et al. "Histamine H4 receptor mediates eosinophil chemotaxis with cell shape change and adhesion molecule upregulation." British journal of pharmacology 142.1 (2004): 161-171.

Damaj, Bassam B., et al. "Functional expression of H4 histamine receptor in human natural killer cells, monocytes, and dendritic cells," The Journal of Immunology 179.11 (2007): 7907-7915.

Cogú, Francis, et al. "Structure and Expression of the Human Histamine H4 Receptor Gene." Biochemical and biophysical research communications 284.2 (2001): 301-309.

Thurmond, Robin L., et al. "A potent and selective histamine H4 receptor antagonist with anti-inflammatory properties." Journal of Pharmacology and Experimental Therapeutics 309.1 (2004): 404-413.

Kirby, John G., et al. "Bronchoalveolar cell profiles of asthmatic and nonasthmatic subjects." American Review of Respiratory Disease 136.2 (1987): 379-383.

Crimi, Emanuele, et al. "Increased numbers of mast cells in bronchial mucosa after the late-phase asthmatic response to allergen." Am Rev Respir Dis 144.6 (1991): 1282-1286.

Amin, Kawa, et al. "Inflammation and structural changes in the airways of patients with atopic and nonatopic asthma," American journal of respiratory and critical care medicine 162.6 (2000): 2295-2301.

Gauvreau, Gail M., et al. "Increased numbers of both airway basophils and mast cells in sputum after allergen inhalation challenge of atopic asthmatics." American journal of respiratory and critical care medicine 161.5 (2000): 1473-1478.

Kassel, Olivier, et al. "Local increase in the number of mast cells and expression of nerve growth factor in the bronchus of asthmatic patients after repeated inhalation of allergen at low-dose." Clinical & Experimental Allergy 31.9 (2001): 1432-1440.

Buckland, Karen F., Timothy J. Williams, and Dolores M. Conroy. "Histamine induces cytoskeletal changes in human eosinophils via the H4 receptor." British journal of pharmacology 140.6 (2003): 1117-1127.

Gutzmer, Ralf, et al. "Histamine H4 receptor stimulation suppresses IL-12p70 production and mediates chemotaxis in human monocyte-derived dendritic cells." the Journal of Immunology 174.9 (2005): 5224-5232.

Mashikian, Margaret Vallen, et al. "Identification of IL-16 as the lymphocyte chemotactic activity in the bronchoalveolar lavage fluid of histamine-challenged asthmatic patients." Journal of allergy and clinical immunology 101.6 (1998): 786-792.

Krug et al., "Interleukin 16 and T-cell Chemoattractant Activity in Bronchoalveolar Lavage 24 Hours after Allergen Challenge in Asthma", American Journal of Respiratory and Critical Care Medicine, vol. 162, No. 1 (2000), pp. 105-111.

Yu, Fuqu, et al. "Pharmacological characterization of oxime agonists of the histamine H4 receptor." J. Receptor Ligand Channel Res 3 (2010): 37-49.

Dunford, Paul J., et al. "Histamine $H_4$ receptor antagonists are superior to traditional antihistamines in the attenuation of experimental pruritus." Journal of allergy and clinical immunology 119.1 (2007): 176-183.

Yamaura, Katsunori, et al. "Expression of histamine H4 receptor in human epidermal tissues and attenuation of experimental pruritus using H4 receptor antagonist." the Journal of toxicological sciences 34.4 (2009): 427-431.

Roβbach, Kristine, et al. "Histamine H4 receptor antagonism reduces hapten-induced scratching behaviour but not inflammation." Experimental dermatology 18.1 (2009): 57-63.

Cowden, Jeffrey M. et al., Journal of Investigative Dermatology "The Histamine $H_4$ Receptor Mediates Inflammation and Pruritus in Th2-Dependent Dermal Inflammation" (2010) 130, 1023-1033; doi:10.1038/jid.2009.358; published online Nov. 12, 2009.

Kiss, Róbert, and György M. Keserü. "Histamine H4 receptor ligands and their potential therapeutic applications: an update." Expert opinion on therapeutic patents 22.3 (2012): 205-221.

Leonardi, A., et al. "Histamine H4 receptors in normal conjunctiva and in vernal keratoconjunctivitis." Allergy 66.10 (2011): 1360-1366.

Massari, N. A., et al. "Role of H4 receptor in histamine-mediated responses in human melanoma." Melanoma research 21.5 (2011): 395.

Medina, V. A., et al. "Role of histamine H4 receptor in breast cancer cell proliferation." Frontiers in bioscience (Elite edition) 3 (2010): 1042-1060.

Fang, Zhengyu, et al. "Attenuated expression of HRH4 in colorectal carcinomas: a potential influence on tumor growth and progression." BMC cancer 11.1 (2011): 195.

Frommberger, Ulrich H., et al. "Interleukin-6-(IL,6) plasma levels in depression and schizophrenia: comparison between the acute state and after remission." European archives of psychiatry and clinical neuroscience 247.4 (1997): 228-233.

Sluzewska, Anna, et al. "Indicators of immune activation in major depression." Psychiatry research 64.3 (1996): 161-167.

O'Brien, Sinead M., et al. "Cytokine profiles in bipolar affective disorder: focus on acutely ill patients." Journal of affective disorders 90.2 (2006): 263-267.

Anisman et al., Interleukin-1β production in dysthymia before and after pharmacotherapy Biological Psychiatry 1999; 46:1649-1655.

Kling, Mitchel A., et al. "Sustained low-grade pro-inflammatory state in unmedicated, remitted women with major depressive disorder as evidenced by elevated serum levels of the acute phase proteins C-reactive protein and serum amyloid A." Biological psychiatry 62.4 (2007): 309-313.

O'Brien, Sinead M., et al. "Plasma cytokine profiles in depressed patients who fail to respond to selective serotonin reuptake inhibitor therapy." Journal of psychiatric research 41.3 (2007): 326-331.

Soygur, Haldun, et al. "Interleukin-6 levels and HPA axis activation in breast cancer patients with major depressive disorder," Progress in Neuro-Psychopharmacology and Biological Psychiatry 31.6 (2007): 1242-1247.

Strakhova, Marina I., et al. "Localization of histamine $H_4$ receptors in the central nervous system of human and rat." Brain research 1250 (2009): 41-48.

Altenbach, Robert J., et al. "Structure-activity studies on a series of a 2-aminopyrimidine-containing histamine H4 receptor ligands," Journal of medicinal chemistry 51.20 (2008): 6571-6580.

Coruzzi, Gabriella, et al. "Antiinflamrnatory and antinociceptive effects of the selective histamine H4receptor antagonists JNJ7777120 and VUF6002 in a rat model of carrageenan-induced acute inflammation." European journal of pharmacology 563.1 (2007): 240-244.

Cowart, Marlon D., et al. "Rotationally constrained 2, 4-diamino-5, 6-disubstituted pyrimidines: a new class of histamine H4 receptor antagonists with improved druglikeness and in vivo efficacy in pain and inflammation models." Journal of medicinal chemistry 51.20 (2008): 6547-6557.

Hsieh, Gin C., et al. "$H_4$ receptor antagonism exhibits anti-nociceptive effects in inflammatory and neuropathic pain models in rats." Pharmacology Biochemistry and Behavior 95.1 (2010): 41-50.

Liu, Huaqing, et al. "cis-4-(Piperazin-1-yl)-5, 6, 7a, 8, 9, 10, 11, 11a-octahydrobenzofuro [2, 3-h] quinazolin-2-amine (A-987306), a new histamine H4R antagonist that blocks pain responses against carrageenan-induced hyperalgesia," Journal of medicinal chemistry 51.22 (2008): 7094-7098.

Nathan, C. Nature; v:420 i:6917 p. 846-852; 2002 Nature Publishing Group.

Tracey, Kevin J. "The inflammatory reflex." Nature 420.6917 (2002): 853-859.

Coussens, Lisa M., and Zena Werb. "Inflammation and cancer." Nature 420.6917 (2002): 860-867.

Libby, Peter, "Inflammation in atherosclerosis" Nature 420.6917 (2002): 868-874.

Benoist, C., "Mast cells in autoimmune disease", Nature 420.6917 (2002): 875-878.

Weiner, Howard L., "Inflammation and therapeutic vaccination in CNS diseases", Nature 420.6917 (2002): 879-884.

(56) References Cited

OTHER PUBLICATIONS

Cohen, Jonathan, "The immunopathogenesis of sepsis", Nature 420. 6917 (2002): 885-891.
Steinberg, Daniel. "Atherogenesis in perspective: hypercholesterolemia and inflammation as partners in crime." Nature medicine 8.11 (2002): 1211-1217.
Berge, Stephen M., et al., "Pharmaceutical salts." Journal of Pharmaceutical Sciences 66.1 (1977): 1-19.
Krogsgaard-Larsen, Povl. A textbook of drug design and development, Harwood Academic Pub, 1991.
O'Reilly, M., et al., J. Recept. Signal Transduction 2002, 22(1-4), 431-448.
Alfon, et al., Inflamm. Res. 2010; 59 (Suppl 2): S199-200.
Ye, F. et al., 2014 ARVO Meeting Abstract, Program #/3291, Board #C0223, Histamine Receptor H4 as a New Therapeutic Target for Choroidal Neovascularization in Age-related macular degeneration).
Gill, D. S., C. S. Thompson, and P. Dandona. "Increased histamine in plasma and tissues in diabetic rats" Diabetes research (Edinburgh, Scotland) 7.1 (1988): 31-34.
Rosa, A. C., et al. "Overexpression of histamine H4 receptors in the kidney of diabetic rat." Inflammation Research 62.4 (2013): 357-365.
Bundgaard, Hans, ed. Design of prodrugs. Elsevier Publishing Company, 1985.
Bundgaard, Hans. "(C) Means to enhance penetration:(1) Prodrugs as a means to improve the delivery of peptide drugs." Advanced Drug Delivery Reviews 8.1 (1992): 1-38.
Bell, J. K., D. S. McQueen, and J. L. Rees. "Involvement of histamine H4 and H1 receptors in scratching induced by histamine receptor agonists in BalbC mice." British Journal of Pharmacology 142.2 (2004): 374-380.
Kaneko et al., "Histamine J4 receptor as a new therapeutic target for choroidal neovascularization in age-related macular degeneration", Bristish Journal of Pharmacology 171 (2014) 3754-3763.
Moorman, Alec J., et al. "In patients with heart failure elevated soluble TNF-receptor 1 is associated with higher risk of depression." Journal of cardiac failure 13.9 (2007): 738-743.
Fokkens, W.J. et al., "Dynamics of mast cells in the nasal mucosa of patients with allergic rhinitis and non-allergic controls: a biopsy study", Clinical & Experimental Allergy, 22(7), 701-710.
Matsuda, N., et al., "Up-Regulation of Histamine H4 Receptors Contributes to Splenic Apoptosis in Septic Mice: Counteraction of the Antiapoptotic Action of Nuclear Factor-κB", J. Pharmacol. Exp. Ther., 2010, 332, 730-737.
Ortiz-Dominguez, et al., "Immune variations in bipolar disorder: phasic differences", Bipolar Disorders 2007: 9: 596-602.
Kim, Yong-Ku et al., "Cytokine imbalance in the pathophysiology of major depresseive disorder", Progress in Neuro-Psychopharmacology & Biological Psychiatry 31 (2007) 1044-1053.
Stahl & Wermuth Handbook of Pharmaceutical Salts, Properties, Selection and Use Stahl and Wermuth eds Wiley-VCH and VHCA Zurich 2002.
U.S. Appl. No. 60/971,676, filed Sep. 12, 2007, Gaul et al.
U.S. Appl. No. 60/972,589, filed Sep. 14, 2007, Edwards.
U.S. Appl. No. 61/014,572, filed Oct. 18, 2007, Kindrachuk.
Aarons, Cary B., et al., Annals of Surgery, 2007, 245, (2), 176-184, "Statins HHMG-CoA Reductase Inhibitors) Decrease Posoperative Adhesions by Increasing Peritoneal Fibrinolytic Activity."
Adachi, S. et al., "The Prevention of Postoperative Intraperitoneal Adhesions by Tranilast: N-(3',4'-dimethoxycinnamoyl) Anthranilic Acid", Surgery Today, Jpn J. Surg. (1999) 29:51-54.
Alberola et al., "Based-Induced Ring Cleavage of 4-Functionalized 3-Unsubstituted Isoxazoles. Synthesis of 2-Aminopyrimidines and Pyrimidine-2(3H)-Thiones", National Taiwan University Library, vol. 25, 1987, pp. 393-397.
Avsar, A.F. et al., "Dyphenhydramine and hyaluronic acid derivatives reduce adnexal adhesions and prevent tubal obstructions in rats", European Journal of Obstetrics & Gynecology and Reproductive Biology 2003, vol. 106, pp. 50-54.
Bäumer, Wolfgang, et al., International Symposium on Atopic Dermatitis, Munich, Germany "Lack of preventing effect of systemically and topically administered histamine $H_4$ receptor antagonists in a canine model of atopic dermatitis" Jul. 22, 2010.
Bäumer, W., et al., "Histamine H1 and H4 Receptor Antagonists Do Not Prevent Acute Skin Lesions in a Canine Model of Atopic Dermatitis", European Histamine Research Society Meeting Sochi, Russia May 12, 2011, Oral Presentation.
Baumer, W., et. al., "Lack of preventing effect of systemically and topically administered histamine H1 or H4 receptor antagonists in a dog model of acute atopic dermatitis", Experimental Dermatology, 2011, pp. 1-5.
Bell et al "Involvement of Histamine $H_4$ and $H_1$ Receptors in Scratching Induced by Histamine Receptor Agonists in BalbC Mice" Br J Pharmaol 2004 vol. 142(2) pp. 374-380.
Bhatt, H. G. et al., "Histamine H4 Receptor: A Novel Therapeutic Target for Immune and Allergic Responses", Mini-Reviews in Medicinal Chemistry, 2010, 10, 1293-1308.
Brown, et al.,Journal of the Chemical Society [Section C], Organic, 1967, (19), 1928-1933.
Cheng et al. "Relationship Between the Inhibition Constant ($K_1$) and the Concentration of Inhibitor Which Causes 50 Percent Inhibition ($I_{50}$) of an Enzymatic Reaction" Biochem Pharmacol 1973 vol. 22 pp. 3099-3108.
Cheong, et al., "Peritoneal Healing and Adhesion Formation/Reformation," Human Reproduction Update, vol. 7, No. 6, pp. 556-566 (2001).
www.clinicaltrials.gov, "A Phase 2b Randomized, Double-blind, Placebo-controlled, Parallel Group, Dose Range Finding Study of JNJ-38518168 in Subjects with Active Rheumatoid Arthritis Despite Concomitant Methotrexate therapy", downloaded Jul. 23, 2014.
www.clinicaltrials.gov, "A Phase 2a Randomized, Double-blind, Placebo-controlled, Multicenter, Parallel Group Study of JNJ-38518168 in Adult Subjects with Uncontrolled, Persistent Asthma", downloaded Jul. 23, 2014.
Cowden, J. M.; et al., The Histamine H4 Receptor Mediates Inflammation in Th2-dependent Dermal Inflammation European Histamine Research Society Meeting, Fulda, Germany May 14, 2009.
Cowden, J.M. et al., "Antagonism of the Histamine $H_4$ Receptor Reduces LPS-induced TNF Production In Vivo", European Histamine Research Society Meeting, Belfast, UK May 4, 2012.
Cowden, J.M. et al., "The Histamine $H_4$ Receptor Mediates Inflammation in Models of Arthritis via Inhibition of Th17", International Congress of Immunology, Milan, Italy Aug. 27, 2013.
Cowden, J. M., et al., Antagonism of the histamine H4 receptor reduces LPS-induced TNF production in vivo, Inflamm. Res. (2013) 62:599-607.
Cowden, J. M., et al., "The histamine H4 receptor mediates inflammation and Th17 responses in preclinical models of arthritis", Ann Rheum Dis 2014;73:600-608.
Desai, P. and Thurmond, R. L., "Histamine H4 receptor activation enhances LPS-induced IL-6 production in mast cells via ERK and PI3K activation", Eur. J. Immunol. 2011. 41: 1764-1773.
Dibb, Karin, et al., "The histamine H4 receptor is a potent inhibitor of adhesion-dependent degranulation in human neutrophils", J. Leukocyte Biol, 2014, vol. 96, p. 1-8.
diZerega, G.S. et al., (1992) Prevention of Postoperative Adhesions in "The Peritoneum" Eds. Springer-Verlag, New York, pp. 307-369.
Dunford, P.J. et al. The histamine H4 receptor mediates allergic airway inflammation by regulating the activation of CD4+ T cells. Journal of Immunology, 2006. vol. 176(11), 7062-7070.
Dunford, P.J., et al., "The Histamine H4 Receptor Drives Inflammation in Preclinical Models of Arthritis", American College of Rheumatology, 2013.
Dunford, P.J., et al., Hansel TT, Barnes PJ (eds): "Histamine H4 receptor antagonists", New Drugs and Targets for Asthma and COPD., Prog Respir Res. Basel, Karger 2010, vol. 39, pp. 187-191.
Edwards, J. P.,"Ten(+) Years of Histamine H4 Antagonists at Janssen", The Scott E. Denmark Symposium, University of Illinios, Urbana-Champaign, IL. Aug. 3, 2013.
Edwards, J. P., "Ten(+) Years of Histamine H4 Antagonists at Janssen", GTC Novel Immunotherapeutics Summit, Jan. 31, 2013.
Edwards, J. P. "What's Out *There*?" University of California, San Diego, Jan. 13, 2014.

(56) References Cited

OTHER PUBLICATIONS

Engelhardt, H. et al., "A New Generation of Anti-Histamines: Histamine H4 Receptor Antagonists on Their Way to the Clinic", Curr. Opin. Drug Disc. Dev., 2009, 12(5), 628-643.
English, et al., Journal of the American Chemical Society, 1946, 68, 1039-1049.
Fei, F., et al., "New substituted benzimidazole derivatives: a patent review (2010-2012)", Expert Opin. Ther. Patents (2013) 23(9).
Horr et al. STAT1 phosphorylation and cleavage is regulated by the histamine (H4) receptor in human atopic and non-atopic lymphocytes. International Immunopharmacology 2006, vol. 6 (10), 1577-1585.
Igel, P., et al., "Histamine H4 receptor agonists", Bioorganic & Medicinal Chemistry Letters, 20 (2010) 7191-7199.
Istyastono, E. P., et al, "Molecular Determinants of Selective Agonist and Antagonist Binding to the Histamine H4 Receptor", Current Topics in Medicinal Chemistry, 2011, 11, 661-679.
Jablonowski, J. et al., The first potent and selective non-imidazole human histamine H4 receptor antagonists. Journal of Medicinal Chemistry, 2003. vol. 46(19), 3957-3960.
Jiang et al. Cloning and pharmacological characterization of the dog histamine H-4 receptor. European Journal of Pharmacology, 2008. vol. 592(1-3), 26-32.
Kamo, A., et al., "Histamine H4 Receptor Antagonists Ineffective against Itch and Skin Inflammation in Atopic Dermatitis Mouse Model", Journal of Investigative Dermatology (2014) 134, 546-548.
Kiss, R. et al. Histamine H4 receptor ligands and their potential therapeutic applications. Expert Opin. Ther. Patents, 2009, vol. 19(2), 119-135.
Róbert Kiss & György M. Keseru, "Novel Histamine H4 Receptor Ligans and Their Potential therapeutic Applications: An Update", Expert Opinion Ther. Patents (2014), vol. 24, pp. 1185-1197.
Kumar et al., "Design, Synthesis and Biological Evaluation of 1,3-diaminopropanes: A new Class of Polyamine Analogs as Leishmanicidal Agents", Bioorg Med Chem Lett, 1997, 7(6), 675-680.
Lee, A. et al., "Development of Benzimidazole Ligands for the H4 Receptor", 229th ACS National Meeting, San Diego, CA, United States, Mar. 13-17, 2005, MEDI-052.
Lee-Dutra, A. et al., Identification of 2-arylbenzimidazoles as potent human histamine H-4 receptor ligands, Bioorganic & Medicinal Chemistry Letters 2006. vol. 16(23), 6043-6048.
Leite-de-Moraes, Cutting edge: histamine receptor H4 activation positively regulates in vivo IL-4 and IFN-gamma production by invariant NKT cells. Journal of Immunology, 2009. 182(3):1233-1236.
Lim, H. et al., Evaluation of histamine H-1-, H-2-, and H-3-receptor ligands at the human histamine H-4 receptor: Identification of 4-methylhistamine as the first potent and selective H-4 receptor agonist. Journal of Pharmacology & Experimental Therapeutics, 2005, vol. 314(3), 1310-1321.
Lim, H.D., et al. "Molecular determinants of ligand binding to H4R species variants" Mol. Pharmacol. 2010, 77 (5), 734-743.
Lim, R., et al., *J Gastrointest Surg* (2008) 12:1754-1761, "An FDA Approved Neurokinin-1 Receptor Antagonist is Effective in Reducing Intraabdominal Adhesions when Administered Intraperitoneally, but Not Orally".
Lochner, S. and Broggini, D. "Impurity Management Progressing from Early to Late Phase Development", 30$^{th}$ SCI Process Development Symposium, Cambridge, England, Dec. 7, 2012.
Charles M. Marson, "Targeting the Histamine H4 Receptor", Chem. Rev. 2011, 111, 7121-7156.
Saskia Nijmeijer et al, "Molecular pharmacology of histamine H4 receptors", Frontiers in Bioscience, 17, 2089-2106, Jun. 1, 2012.
Onuma, S."Usefulness of the histamine $H_4$ receptor antagonist on exacerbation of pruritus induced by long-term topical steroids treatment", Japanese Society of Toxicology Jul. 2-4, 2014.
Parsons et al. " Histamine and Its Receptors" British Jurnal of Pharmacology 2006 vol. 147 pp. S127-S-135.

Popov, A. et al., "Spontaneous Gelation of a Novel Histamine H4 Receptor Antagonist in Aqueous Solution", Pharm Res (2011) 28:2556-2566.
Practice Committee of the American Society for Reproductive Medicine in collaboration with the Society of Reproductive Surgeons, Fertility and Sterility, 2013, 99,( 6), 1550-1555, "Pathogenesis, consequences, and control of peritoneal adhesions in gynecologic surgery: a committee opinion".
Robinson Malcom, "Medical Therapy of Inflammatory Bowel Disease for the 21$^{st}$ Century" Eur J. Surg 1998 Suppl 582 pp. 90-98.
Rodgers, K.E., et al., (1990) "Nonsteroidal Anti-Inflammatory Drugs (NSAIDs) in the treatment of Postsurgical Adhesion" Treatment of Post-Surgical Adhesions, pp. 119-129.
Savall, B.M., et al. "Agonist/antagonist modulation in a series of 2-aryl benzimidazole H4 receptor ligands" Bioorg Med Chem Lett, 2010, 20(11), 3367-3371.
Savall, B.M. et al., "6-Alkyl-2-aminopyrimidines as Potent Histamine H4 Receptor Antagonists", Gordon Research Conference Medicinal Chemistry, Aug. 5-10, 2012.
Savall, B.M., et al., Selective phenol alkylation for an improved synthesis of 2-arylbenzimidazole H4 receptor ligands, Tetrahedron Letters 50 (2009) 2490-2492.
Savall, B. M., et al., "Discovery and SAR of 6-Alkyl-2,4-diaminopyrimidines as Histamine H4 Receptor Antagonists", J. Med. Chem. 2014, 57(6), 2429-2439.
Savall, B. M. et al., "Tricyclic aminopyrimidine histamine H4 receptor antagonists", Bioorganic & Medicinal Chemistry Letters 21 (2011) 6577-6581.
Schneider E.H., et al. "Structural requirements for inverse agonism and neutral antagonism of indole-, benzimidazole-, and thienopyrrole-derived histamine H4 receptor ligands" J. Pharmacol Exp Ther 2010, 334 (2) 513-521.
Short et al., "Sympathetic Nervous System Blocking Agents. Derivatives of Guanidine and Related Compounds." J. Med. Chem., 1963, 6, 275-283.
Siegel et al, "Rapid Parallel Synthesis Applied to the Optimization of a Series of Potent Nonpeptide Neuropeptide Y-1 Receptor Antagonists", *Tetrahedron* (1995) 55:11619-11639.
Silverman Richard B. "Prodrugs and Drug Delivery Systems" The Organic Chemistry of Drug Design and Drug Action 1997 Chapter 8 pp. 353-399.
Singh et al. "Immune Therapy in Inflammation Bowel Disease and Models Colitis" British Journal of Surgery 2001 vol. 88 pp. 1558-1569.
Slater et al "Increase in epithelial Mast Cell Numbers in the Nasal Mucosa of Patients with Perennial Allergic Rhinitis" J Laryngol Otol 1996 vol. 110 pp. 929-933.
Smits, R.A. et al. Major advances in the development of histamine H4 receptor ligands. Drug Discovery Today, 2009, vol. 14(15-16):745-753.
Song et al, "Synthesis of Cyclic Prodrugs of Aggrastat and Its Analogue with a Modified Phenylpropionic Acid Linker", *Organic Letters* (2002) 4(4):549-552.
Stark, H. (editor), "Histamine H4 Receptor: A Novel Drug Target for Immunoregulation and Inflamation", Walter de Gruyter & Co (Dec. 2, 2013), Chapter 2, Schreeb, A. et al., Histamine H4 Receptor Ligands.
Takeshita et al "Critical Role of Histamine $H_4$ Receptor in Leukotriene B4 Production and Mast-Cell Dependent Neutrophil Recruitment Induced by Zymosan in Vivo" J Pharmacol Exp Ther 2003 vol. 307(3) pp. 1072-1078.
Terzioglu et al. "Synthesis and Structure-Activity Relationship of Indole and Benzimidazole Piperazines as Histamine $H_4$ Receptor Antagonists" Bioorg & Med Chemistry Letters 2004 vol. 14 pp. 5251-5256.
Testa et al "Predicting Drug Metabolism: Concepts and Challenges" Pure Appl Chem 2004 vol. 76(5) pp. 907-914.
Thurmond, R. L.; "Histamine $H_4$ Receptor Antagonists as Future Anti-Inflammatory Drugs", European Academy of Allergology and Clinical Immunology, London, UK Jun. 8, 2010.
Thurmond, R. L.; "The Role of the Histamine $H_4$ Receptor in Allergy and Inflammation", European Histamine Research Society Meeting Sochi, Russia May 13, 2011.

(56) References Cited

OTHER PUBLICATIONS

Thurmond, R. L.; "Clinical Development of Histamine $H_4$ Receptor Antagonists", Lecture at University of Hanover, Germany May 12, 2014.

Thurmond, R. L.; "The Role of the Histamine $H_4$ Receptor in Allergy and Inflammation", Lecture at University of Hanover, Germany May 17, 2011.

Thurmond, R. L.; "The Histamine $H_4$ Receptor and Immune Function", Japanese Society of Immunotoxicity, Chiba, Japan Sep. 8, 2011.

Thurmond, R. L.; "Frontiers in Histamine Research", American Academy of Allergy, Asthma and Immunology, San Francisco, CA, Mar. 18-22, 2011.

Thurmond, R. L.; "The Role of the Histamine H4 Receptor in Allergy and Inflammation", Allergy Drug Discovery and Development Conference, San Diego, CA Jan. 30, 2012.

Thurmond, R. L.;" Novel Antihistamines that Target the Histamine $H_4$ Receptor", Experimental Biology Meeting, San Diego, CA, Apr. 22, 2012.

Thurmond, R.L., "The Development of Histamine $H_4$ Receptor Antagonists", Japanese Society of Toxicology Chiba Japan Jun. 18, 2013.

Thurmond, R. L. et al., "The Histamine $H_4$ Receptor Mediates Inflammation and Pruritus in Th2-dependent Dermal Inflammation", International Congress of Immunology, Kobe, Japan Aug. 22-27, 2010.

Thurmond, R. L.; "Histamine H4 Receptor Antagonists New Antihistamines for Itch", 21st Annual Meeting of the International Symposium of Itch,Osaka, Japan Oct. 29, 2011.

Thurmond, R. L.; "The Role of the Histamine H4 Receptor in Allergy and Inflammation", Lecture at University of Vermont, Burlington, VT Nov. 5, 2010.

Thurmond, R. L.; "The Histamine H4 Receptor and Immune Function", Lecture at Tohoku University Sendai, Japan Sep. 7, 2011.

Thurmond, R. L.; "The Role of the Histamine H4 Receptor in Allergy and Inflammation", Lecture at Queen's University Belfast, UK May 1, 2012.

Thurmond, R. L.; "Histamine H4 Receptor Antagonists as Future Anti-Inflammatory Drugs", 27th Noordwijkerhout-Camerino-Cyprus Symposium, Noordwijkerhout, Netherlands, May 5, 2009.

Thurmond, R. L., et al, "Clinical and Preclinical Characterization of the Histamine H4 Receptor Antagonist JNJ-39758979", J Pharmacol Exp Ther 349:176-184, May 2014.

Mitsutoshi Tominaga, "Histamine $H_4$ receptor antagonists ineffective against itch and skin inflammation in atopic dermatitis mouse model", $7^{th}$ World Congress on Itch (WCI) Sep. 21-23, 2013, Boston, USA, Oral Presentation, Abstract provided.

Mitsutoshi Tominaga. International Investigative Dermatology, "Histamine $H_4$ receptor antagonists exhibit insufficient anti-pruritic and anti-inflammatory effects on mite extract ointment-induced mouse model of atopic dermatitis", May 8-11, 2013, Edinburgh, Scotland, Oral Presentation, Abstract provided.

Mitsutoshi Tominaga , "Histamine $H_4$ receptor antagonists exhibit insufficient anti-pruritic and anti-inflammatory effects on mite extract ointment-induced mouse model of atopic dermatitis", International Investigative Dermatology, May 8-11, 2013, Edinburgh, Scotland.

Ulrich, J and Stelzer, T. (2001) Kirk-Othmer Encyclopedia of Chemical Technology, "Crystallization", 1-63.

Ural, A.U. et al., *Annals of Surgery*, 2008, 247, (1), 203-205, "Bisphosphonates May Increase Peritoneal Fibrinolytic Activity by Inhibiting the Mevalonate Pathway".

Two application statements on a non-proprietary name adopted by the USAN Council dated May 28, 2014.

Varga et al "Inhibitory Effects of Histamine $H^4$ Receptor Antagonists on Experimental Colitis in the Rat" Eur J Pharmacol 2005 vol. 522(1-3) pp. 130-138.

Venable, J.D. et al. Preparation and biological evaluation of indole, benzimidazole, and thienopyrrole piperazine carboxamides: Potent human histamine $H_4$ antagonists. Journal of Medicinal Chemistry, 2005. vol. 28(26), 8289-8298.

Venable, J.D., et al. "Development and chemistry of histamine H4 receptor ligands as potential modulators of inflammatory and allergic diseases" Anti-Inflamm Anti-Allergy Agents in Med Chem. 2006, 5 (4), 307-322.

Venable, J. "Discovery, SAR, and functional consequences of various 2-heteroarylbenzimidazoles at the human histamine H4 receptor of 2-heteroarylbenzimidazoles", 67th Southwest Regional Meeting of the American Chemical Society, Austin, TX, United States, Nov. 9-12, 2011, SWRM-183.

Venable, J. "Synthesis and SAR of 2-Pyridinylbenzimidazoles as Human Histamine $H_4$ Antagonists", CHI Drug Discovery Chemistry, Apr. 27-28, 2010 • San Diego, CA.

Venable , J, "Novel Modulators of the Human Histamine $H_4$ Receptor", California Institute of Technology, Pasadena, California Apr. 6, 2011.

Venable, J, "Discovery and Development of Human Histamine $H_4$ Antagonists", Medicinal Chemistry Symposium, University of California, San Diego, Jul. 12, 2013.

Venable J., "Synthesis and SAR of 2-Pyridinylbenzimidazoles as Human Histamine $H_4$ Antagonists", 239th ACS National Meeting, San Francisco, CA, United States, Mar. 21-25, 2010, MEDI-14.

Walter, M., et al., "Histamine receptor subtypes: a century of rational drug design", Frontiers in Bioscience S4, 461-488, Jan. 1, 2012.

Katsunori Yamaura, Joint Symposium of the Japanese Society of Toxicology and the Japanese Society of Immunotoxicology, "Long-term topical steroids treatment and skin toxicity characterized by pruritus" Jul. 2014, Oral Presentation.

Yildiz, M.K., et al., *Int J Clin Exp Med*. 2014; 7(2): 405-410, "Effect of orally administered simvastatin on prevention of postoperative adhesion in rats".

Zhichkin et al. "A General Procedure for the Synthesis of 2-Substituted Pyrimidine-5-Carboxylic Esters" Synthesis 2002 vol. 6 pp. 720-722.

Jack D. Dunitz and Joel Bernstein, "Disappearing Polymorphs", Acc. Chem. Res., 1995, Vol. 28, No. 4, pp. 193-200.

John K. Haleblian and Walter McCrone, "Pharmaceutical Applications of Polymorphism", Journal of Pharmaceutical Sciences, 1969, Vol. 58, No. 8, pp. 911-929.

John K. Haleblian, "Characterization of Habits and Crystalline Modification of Solids and Their Pharmaceutical Applications", Journal of Pharmaceutical Sciences, 1975, Vol. 64, No. 8, pp. 1269-1288.

Search Report Issued by the Intellectual Property Corporation of Malaysia Dated October 23, 2014 for Corresponding Application No. PI 2010006259.

Slater, A., et al., "Increase in epithelial mast cell numbers in the nasal mucosa of patients with perennial allergic rhinitis", Journal of Laryngology and Otology, Oct. 1996, vol. 110, pp. 929-933.

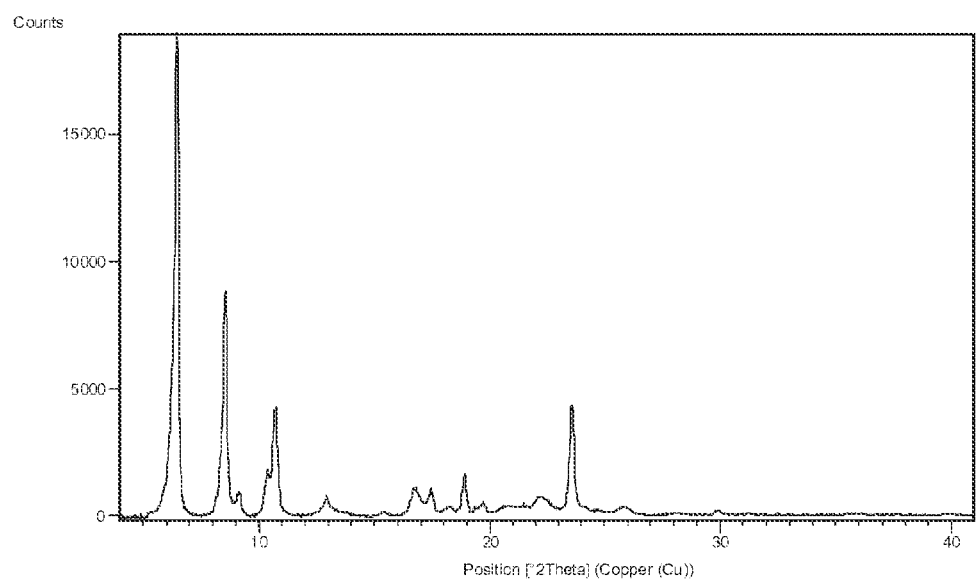
Powder XRD pattern for a sample of crystalline hemi-tartrate of compound of formula (I-A).

BENZOIMIDAZOL-2-YL PYRIMIDINE DERIVATIVES

This application is a continuation-in-part of U.S. application Ser. No. 13/427,798, filed on Mar. 22, 2012, which is a divisional application of U.S. application Ser. No. 12/459,224, filed on Jun. 29, 2009, now abandoned, which claims the benefit of U.S. Provisional Application 61/076,759, filed on Jun. 30, 2008.

FIELD OF THE INVENTION

The present invention is directed to benzoimidazol-2-yl pyrimidine derivatives useful as histamine $H_4$ receptor modulators and processes for the preparation of such compounds.

BACKGROUND OF THE INVENTION

The histamine $H_4$ receptor ($H_4R$), sometimes also referred to simply as "H4" or "$H_4$", is the most recently identified receptor for histamine (for reviews, see: Fung-Leung, W.-P., et al., Curr. Opin. Invest. Drugs 2004, 5(11), 1174-1183; de Esch, I. J. P., et al., Trends Pharmacol. Sci. 2005, 26(9), 462-469; Zhang, M. et al. Pharmacol. Ther. 2007, 113, 594-606; Thurmond, R. L. et al. Nat. Rev. Drug Disc. 2008, 7, 41-53; Zhang, M. et al. Expert Opin. Investig. Drugs 2006, 15(11), 1443-1452). The receptor is found in the bone marrow and spleen and is expressed on eosinophils, basophils, mast cells (Liu, C., et al., Mol. Pharmacol, 2001, 59(3), 420-426; Morse, K. L., et al., J. Pharmacol. Exp. Ther. 2001, 296(3), 1058-1066; Hofstra, C. L., et al., J. Pharmacol. Exp. Ther. 2003, 305(3), 1212-1221; Lippert, U., et al., J. Invest. Dermatol. 2004, 123(1), 116-123; Voehringer, D., et al., Immunity 2004, 20(3), 267-277), $CD8^+$ T cells (Gantner, F., et al., J. Pharmacol. Exp. Ther. 2002, 303(1), 300-307), dendritic cells, and human synovial cells from rheumatoid arthritis patients (Ikawa, Y., et al., Biol. Pharm. Bull. 2005, 28(10), 2016-2018). The histamine $H_4$ receptor is also elevated in human nasal polyp tissue (Jókúti, A. et al. Cell. Biol. Int. 2007, 31, 1367-1370). However, expression in neutrophils and monocytes is less well defined (Ling, P., et al., Br. J. Pharmacol. 2004, 142(1), 161-171; Damaj, B. B. et al. J. Immunol. 2007, 179, 7907-7915). Receptor expression is at least in part controlled by various inflammatory stimuli (Coge, F., et al., Biochem. Biophys. Res. Commun. 2001, 284(2), 301-309; Morse, et al., 2001), thus supporting that $H_4$ receptor activation influences inflammatory responses. Because of its preferential expression on immunocompetent cells, the $H_4$ receptor is closely related with the regulatory functions of histamine during the immune response.

A biological activity of histamine in the context of immunology and autoimmune diseases is closely related with the allergic response and its deleterious effects, such as inflammation. Events that elicit the inflammatory response include physical stimulation (including trauma), chemical stimulation, infection, and invasion by a foreign body. The inflammatory response is characterized by pain, increased temperature, redness, swelling, reduced function, or a combination of these.

Mast cell degranulation (exocytosis) releases histamine and leads to an inflammatory response that may be initially characterized by a histamine-modulated wheal and flare reaction. A wide variety of immunological stimuli (e.g., allergens or antibodies) and non-immunological (e.g., chemical) stimuli may cause the activation, recruitment, and de-granulation of mast cells. Mast cell activation initiates allergic inflammatory responses, which in turn cause the recruitment of other effector cells that further contribute to the inflammatory response. It has been shown that histamine induces chemotaxis of mouse mast cells (Hofstra, et al., 2003). Chemotaxis does not occur using mast cells derived from $H_4$ receptor knockout mice. Furthermore, the response is blocked by an $H_4$-specific antagonist, but not by $H_1$, $H_2$ or $H_3$ receptor antagonists (Hofstra, et al., 2003; Thurmond, R. L., et al., J. Pharmacol. Exp. Ther. 2004, 309(1), 404-413). The in vivo migration of mast cells to histamine has also been investigated and shown to be $H_4$ receptor dependent (Thurmond, et al., 2004). The migration of mast cells may play a role in allergic rhinitis and allergy where increases in mast cell number are found (Kirby. J. G., et al., Am. Rev. Respir. Dis. 1987, 136(2), 379-383; Crimi, E., et al., Am. Rev. Respir. Dis. 1991, 144(6), 1282-1286; Amin, K., et al., Am. J. Resp. Crit. Care Med. 2000, 162(6), 2295-2301; Gauvreau, G. M., et al., Am. J. Resp. Crit. Care Med. 2000, 161(5), 1473-1478; Kassel, O., et al., Clin. Exp. Allergy 2001, 31(9), 1432-1440). In addition, it is known that in response to allergens there is a redistribution of mast cells to the epithelial lining of the nasal mucosa (Fokkens, W. J., et al., Clin. Exp. Allergy 1992, 22(7), 701-710; Slater, A., et al., J. Laryngol. Otol. 1996, 110, 929-933). These results show that the chemotactic response of mast cells to histamine is mediated by histamine $H_4$ receptors.

It has been shown that eosinophils can chemotax towards histamine (O'Reilly, M., et al., J. Recept. Signal Transduction 2002, 22(1-4), 431-448; Buckland, K. F., et al., Br. J. Pharmacol. 2003, 140(6), 1117-1127; Ling et al., 2004). Using $H_4$ selective ligands, it has been shown that histamine-induced chemotaxis of eosinophils is mediated through the $H_4$ receptor (Buckland, et al., 2003; Ling et al., 2004). Cell surface expression of adhesion molecules, CD11b/CD18 (LFA-1) and CD54 (ICAM-1), on eosinophils increases after histamine treatment (Ling, et al., 2004). This increase is blocked by $H_4$ receptor antagonists but not by $H_1$, $H_2$, or $H_3$ receptor antagonists.

The $H_4R$ also plays a role in dendritic cells and T cells. In human monocyte-derived dendritic cells, $H_4R$ stimulation suppresses IL-12p70 production and drives histamine-mediated chemotaxis (Gutzmer, R., et al., J. Immunol, 2005, 174 (9), 5224-5232). A role for the $H_4$ receptor in $CD8^+$ T cells has also been reported. Gantner, et al., (2002) showed that both $H_4$ and $H_2$ receptors control histamine-induced IL-16 release from human $CD8^+$ T cells. IL-16 was found in the bronchoalveolar fluid of allergen- or histamine-challenged asthmatics (Mashikian, V. M., et al., J. Allergy Clin. Immunol. 1998, 101 (6, Part 1), 786-792; Krug, N., et al., Am. J. Resp. Crit. Care Med. 2000, 162(1), 105-111) and is considered important in $CD4^+$ cell migration. Cowden et al (Respir Res, 2010; 11:86) showed that blockade of the $H_4$ receptor inhibited T cell infiltration into the lung and decreased Th2 cytokines IL-13 and IL-5. Additionally, improvement in measures of central and peripheral airway dysfunction were shown with $H_4$ antagonists (Alfon, et al., Inflamm Res, 2010; 59 (Suppl 2): S199-200).

There has also been evidence that the histamine $H_4$ receptor ($H_4R$) mediates pruritus in mice, but via a different mechanism from the histamine $H_1$ receptor ($H_1R$), and therefore it may play a role in pruritic responses in atopic dermatitis. In mice, histamine and selective histamine $H_4R$ agonists caused scratching responses, which were almost completely abolished in $H_4R$ knockout mice or by pretreatment with an $H_4R$ antagonist, Yu, F. et al., *Journal of Receptor, Ligand and Channel Research* 3, 37-49 (2010); Dunford, P. J. et al., *Journal of Allergy and Clinical Immunology* 119, 176-183 (2007); Bell, J. K., et al., *British Journal of Pharmacology* 142, 374-380 (2004)). Differential roles for the $H_1R$ and $H_4R$ were observed in mouse models where scratching behavior was induced by histamine or substance P. The $H_1R$ antagonist, fexofenadine, reduced scratching induced by histamine but not by substance P, whereas the same $H_4R$ antagonist significantly reduced both histamine- and substance P-induced scratching, (Yamaura, K, et al., *Journal of Toxicological Sciences* 34, 427-431 (2009)). In addition, the same antagonist was shown to be effective in reducing hapten-induced scratching behavior and scratching to IgE-mediated mast cell degranulation. (Dunford, P. J. et al., *Journal of Allergy and Clinical Immunology* 119, 176-183 (2007); Rossbach, K. et al., *Experimental Dermatology* 18, 57-63 (2009). The same was seen in the mouse model of atopic dermatitis where scratching to the hapten was reduced by $H_4R$ antagonist treatment. (Cowden, J. M., et al., *Journal of Investigative Dermatology* (2009)).

Therefore, based on the above mentioned experimental results, it may be envisaged that $H_4R$ antagonists may have utility for the treatment of itch associated with a variety of conditions such as atopic dermatitis eczema, urticaria (hives), psoriasis, oncological conditions such as T cell lymphoma, itch associated with the administration of drugs to treat parasitic or fungal infections (e.g., lice, scabies, swimmer's itch, jock itch, athlete's foot), hidradenitis suppurativa, malignancy/lymphoma (e.g., Hodgkin's disease), jaundice, polycythemia, punctate palmoplantar keratoderma, thyroid illness/hyperparathyroidism, diabetes, primary biliary cirrhosis, chicken pox, iron deficiency anemia, psychiatric diseases, medication-induced cholestasis; pregnancy-related cholestasis (e.g., obstetric cholestasis), pruritic urticaria papules and plaques of pregnancy, gestational phemphigoid; xerosis (dry skin), sunburn, dandruff, scab/scars, insect bites, poison ivy/oak, hemorrhoids, contact dermatitis, old-age associated itch, and itch associated with dialysis.

Recent work has shown that the $H_4$ receptor and/or $H_4$ modulators (agonists or antagonists) may play a role in a diverse array of medical conditions and diseases. (Kiss, R. and Keseru, G. M., Expert Opin. Ther. Patents, 2012, 22(3), 205-221) Several of which are listed below. The treatment of choroidal neovascularization in age-related macular degeneration (AMD) using $H_4$ antagonists has been investigated. (Ye, F. et al. 2014 ARVO Meeting Abstract, Program #3291, Board #C0223, *Histamine Receptor H4 as a New Therapeutic Target for Choroidal Neovascularization in Age-related Macular Degeneration*). The $H_4$ receptor was also found to be highly expressed in stromal inflammation cells in vernal keratoconjuctivitis (Leonardi, A. et al., Allergy, 2011, 66, 1360-1366.) In addition, studies using $H_4$ antagonists for the treatment of post-operative adhesions were conducted (WO2009152287), and research on the role of H4 receptors and modulators in cancer, for example melanoma, breast cancer and colorectal carcinomas (Massari, N. A. et al. Melanoma Res, 2011, 21, 395-404; Medina, V. A. et al., Front Biosci (Elite Ed), 2011, 3, 1042-1060; Fang, Z. et al., BMC Cancer, 2011, 11:195, 1-11) have also been performed. In a mouse model of sepsis, expression of the $H_4$ receptor gene was significantly up-regulated in key organs including the spleen, implicating a potential therapeutic role of $H_4$ antagonists in the treatment of sepsis. (Matsuda, N., et al., J. Pharmacol. Exp. Ther, 2010, 332, 730-737.) It has also been theorized that $H_4$ antagonists may be administered with a long acting β-agonist, acting in a synergistic manner to improve lung functions and in the treatment of asthma.

Numerous pro-inflammatory cytokines have been increasingly reported to be elevated in patients suffering of major depression, when compared with non-depressed subjects or, in some cases, correlated with symptom severity. (Frommberger et al., European Archives of Psychiatry & Clinical Neuroscience. 1997, 247(4), 228-33; Sluzewska A., et al., Psychiatry Research, 1996, 64(3), 161-7; Ortiz-Dominguez, et al., Bip. Disorder 9, 2007; O'Brien, et al., J. Affective Disorders, 2006, 90, 263-267; Anisman H. et al., Biological Psychiatry, 1999, 46(12),1649-55) These include increased acute-phase proteins (Kling et al., Biol. Psychiatry, 2007, 62, 309-313; Kim et al., Progress in Neuro-Psychopharmacology & Biological Psychiatry, 2007, 31, 1044-1053; (C-reactive protein, α-1-acid glycoprotein, α-1-antichymotrypsin and haptoglobin), increased expression of chemokines and adhesion molecules (including human macrophage chemoattractant protein-1 (MCP-1), soluble intracellular adhesion molecule-1 (sICAM-1) and E-selectin), and increased serum and/or plasma concentrations of interleukin(IL)-1-β, IL-6, and tumor necrosis factor (TNF)-α, both in the peripheral blood circulation and in the central nervous system (particularly in the cerebrospinal fluid) with a higher level of consistency when measuring TNF-α and IL-6 (O'Brien et al., Journal of Psychiatric Research, 2007, 41, 326-331; Moorman et al., J. of Cardiac Failure, 2007, 13(9), 738-43; Soygur et al., Progress in Neuro-Psychopharmacology & Biolofical Psychiatry, 2007, 31, 1242-1247). Additionally, allelic variants of the genes for IL-1β and TNF-α increase the risk for depression and are associated with reduced responsiveness to anti-depressant therapy. Finally, there is available preclinical evidence supporting the involvement of several cytokines in models of depression and some clinical evidence of the involvement of cytokines antagonism in the treatment of depressive symptoms on patients suffering from active inflammatory diseases (Kim et al., (2007)).

Thus, based at least inpart on citations above, it is envisaged that $H_4$ antagonists may have antidepressant and/or anxiolytic properties suitable for the treatment of mood disorders (including but not limited to Major Depressive Disorder, Bipolar Disorder, Treatment Resistant Major Depressive Disorder and Treatment Resistant Bipolar Disorder), anxiety disorders (including but not limited to Generalized Anxiety Disorder, Social Phobia, and post traumatic stress disorder).

Modulation of the histamine $H_4$ receptor has also been implicated in the treatment of pain (Intl. Pat. Appl. Publ. WO 2008/060766 (Abbott). The $H_4R$ has been shown to be expressed in the CNS, including the brain, spinal cord, and dorsal root ganglia. (Strakhova, M. I. et al., *Brain Research* 1250, 41-48 (2009)). $H_4R$ antagonists have been shown to possess antinociceptive activity in several models of pain. (Altenbach, R. J., et al., *J. Med. Chem.* 51, 6571-6580 (2008); Coruzzi, G., et al., *European Journal of Pharmacology* 563, 240-244 (2007); Cowart, M. D. et al., *J. Med. Chem.* 51, 6547-6557 (2008); Hsieh, G. C. et al., *Pharmacol. Biochem. Behav.* 95, 41-50 (2010)). The $H_4R$ antagonist given in example 1, U.S. Pat. No. 6,803,362, was as efficacious as diclofenac in an acute carrageenan-induced inflammatory pain model and in a more chronic CFA-induced pain model. (Hsieh, G. C. et al., (2010)). Similar results were seen in a model of osteoarthritis where the maximum efficacy was on par with celecoxib and in a model of post-operative pain where the efficacy approached that of morphine. (Hsieh, G. C. et al., (2010)). Activity for a number of compounds has been reported in neuropathic pain models including an antagonist wherein the efficacy was superior to that of gabapentin in two different models. (Cowart, M. D. et al., (2008); Hsieh. G. C. et al., (2010)). In addition, selective H₄R antagonists significantly reduced paw edema and hyperalgesia provoked by subplantar injection of carrageenan in a rat acute inflammation and hyperalgesia model. (Coruzzi, G., et al., (2007); Liu, H. et al., *J. Med. Chem.* 51, 7094-7098 (2008)). These data support the claims that H₄R antagonist may have utility in the treatment of nociceptive and/or neuropathic pain.

Adiposity-associated inflammation and insulin resistance are associated with the development of type II diabetes, fatty liver and atherosclerosis. The role of the H₄ receptor and its ligands in these conditions has been explored. (Gill, D. S. Diabetes Research, 1988, 7(1), 31-34; Rosa, A. C., Inflammation Research, 2013, 62(4), 357-365). Macrophages are recruited into adipose tissue and atherosclerotic plaques, and are activated to release inflammatory cytokines and chemokines. High fat diets associated with the development of these conditions may lead to increased gut permeability and dyslipidemia. Consequent toll-ligand receptor, 2 and 4 (TLR2, TLR4) activation of adipocytes and macrophages by bacteria and by high levels of free fatty acids leads to an inflammatory phenotype and insulin resistance. Specifically, insulin signaling pathways may be attenuated by cytokines such as TNFα and IL-6 and activation of kinases including c-jun kinase, NKkB or PKCθ, downstream of TLR2/4 stimulation. Effects on insulin receptor signaling are potentiated by increased infiltration of monocyte/macrophages into the tissue by release of chemokines such as MCP-1.

H₄R is a high affinity receptor for histamine expressed on monocyte/macrophage populations and other hematopoietic cells. Antagonism of the H₄R has been shown to reduce TLR4 signaling in vitro and to reduce TLR2 and TLR4 mediated inflammatory cytokine production in vitro and in vivo. Levels of pro-inflammatory mediators including TNF-α, IL-6 and LTB4 have been variously shown to be inhibited by H₄R antagonism in TLR dependent systems.

Examples of textbooks on the subject of inflammation include: 1) Gallin, J. I.; Snyderman, R., *Inflammation: Basic Principles and Clinical Correlates,* 3rd ed.; Lippincott Williams & Wilkins: Philadelphia, 1999; 2) Stvrtinova, V., et al., Inflammation and Fever. *Pathophysiology Principles of Diseases* (Textbook for Medical Students); Academic Press: New York, 1995; 3) Cecil; et al, *Textbook Of Medicine,* 18th ed.; W.B. Saunders Co., 1988; and 4) Stedman's Medical Dictionary.

Background and review material on inflammation and conditions related with inflammation can be found in articles such as the following: Nathan, C., Nature 2002, 420(6917), 846-852; Tracey, K. J., Nature 2002, 420(6917), 853-859; Coussens, L. M., et al., Nature 2002, 420(6917), 860-867; Libby, P., Nature 2002, 420, 868-874; Benoist, C., et al., Nature 2002, 420(6917), 875-878; Weiner, H. L., et al., Nature 2002, 420(6917), 879-884; Cohen, J., Nature 2002, 420(6917), 885-891; Steinberg, D., Nature Med. 2002, 8(11), 1211-1217.

SUMMARY OF THE INVENTION

The present invention is directed to a process for the preparation of compounds of formula (I), which may be used as H4₄ modulators,

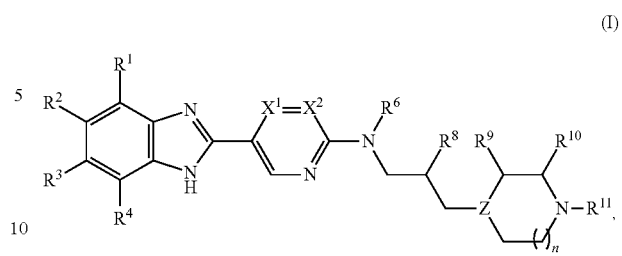

wherein each of $R^1$, $R^2$, $R^3$ and $R^4$ are each independently selected from the group consisting of H, $C_{1-4}$alkyl, $C_{2-4}$alkenyl, $C_{2-4}$alkynyl, phenyl, —$CF_3$, —$OCF_3$, —CN, halo, —$NO_2$, —$OC_{1-4}$alkyl, —$SC_{1-4}$alkyl, —$S(O)C_{1-4}$alkyl, —$SO_2C_{1-4}$alkyl, —$C(O)C_{1-4}$alkyl, —$C(O)$phenyl, —$C(O)NR^aR^b$, —$CO_2C_{1-4}$alkyl, —$CO_2H$, —$C(O)NR^aR^b$, and —$NR^aR^b$; wherein $R^a$ and $R^b$ are each independently selected from the group consisting of H, $C_{1-4}$alkyl, and $C_{3-7}$cycloalkyl;

$X^1$ is C—$R^C$; wherein $R^c$ is selected from the group consisting of H, methyl, hydroxymethyl, dimethylaminomethyl, ethyl, propyl, isopropyl, —$CF_3$, cyclopropyl, and cyclobutyl; and $X^2$ is N;

n is 1 or 2;

Z is selected from the group consisting of N, CH, and C($C_{1-4}$alkyl);

$R^6$ is selected from the group consisting of H, $C_{1-6}$alkyl, and a monocyclic cycloalkyl;

$R^8$ is selected from the group consisting of H and $C_{1-4}$alkyl;

$R^9$, $R^{10}$ and $R^{11}$ are each independently selected from the group consisting of H and $C_{1-4}$alkyl;

and pharmaceutically acceptable salts, pharmaceutically acceptable prodrugs, and pharmaceutically active metabolites thereof; comprising

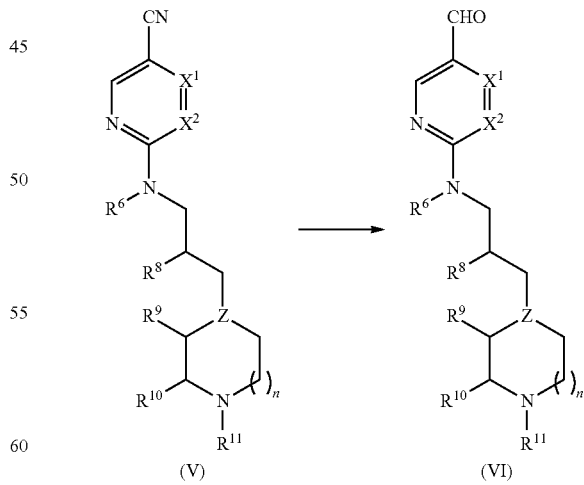

reacting a compound of formula (V) with a reducing agent system; in a solvent; at a temperature in the range of from about 0° C. to about 25° C.; to yield compound of formula (VI); and

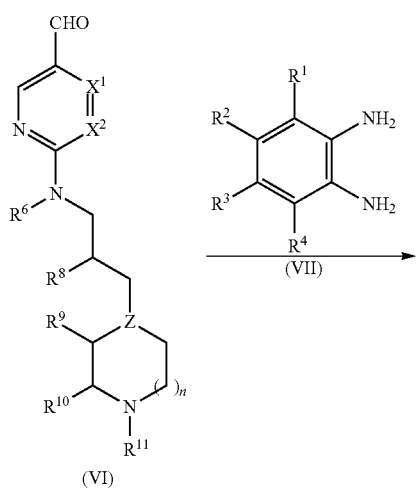

(VI)

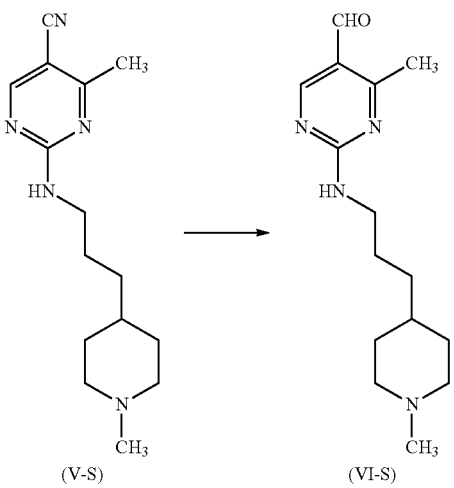 [SMILES: Cc1nc(NCCCC2CCN(C)CC2)ncc1C#N ; Cc1nc(NCCCC2CCN(C)CC2)ncc1C=O ; "(V-S)" ; "(VI-S)"]

(V-S) (VI-S)

reacting a compound of formula (V-S) with a reducing agent system; in a solvent; at a temperature in the range of from about 0° C. to about 25° C., to yield compound of formula (VI-S); and

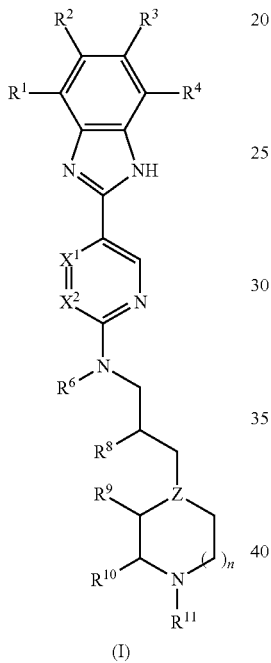

(I)

reacting compound of formula (VI) with a compound of formula (VII); in the presence of a suitably selected oxidizing agent or oxidizing agent system, in water or in an organic solvent, at a temperature in the range of from about 25° C. to about 100° C.

In an embodiment, the present invention is directed to a process for the preparation of a compound of formula (I-A)

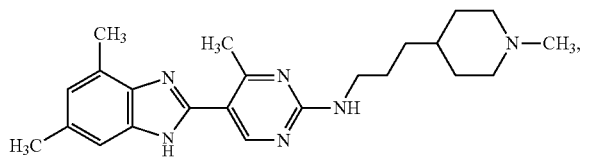

(I-A)

(also known as [5-(4,6-dimethyl-1H-benzoimidazol-2-yl)-4-methyl-pyrimidin-2-yl]-[3-(1-methyl-piperidin-4-yl)-propyl]-amine) or a pharmaceutically acceptable salt, or a pharmaceutically acceptable prodrug, or a pharmaceutically active metabolite thereof; comprising

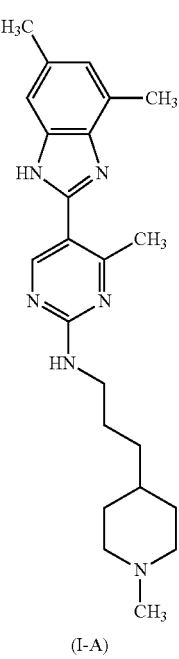

(I-A)

reacting compound of formula (VI-S) with a compound of formula (VII-A); in the presence of a suitably selected oxidizing agent or oxidizing agent system, in water or in an organic solvent, at a temperature in the range of from about 25° C. to about 100° C., to yield compound of formula (I-A).

In another embodiment, the present invention is directed to a process for the preparation of a compound of formula (I-B)

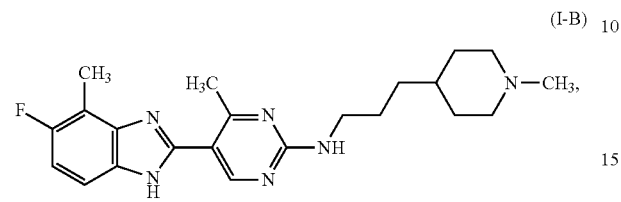

(I-B)

(also known as [5-(5-Fluoro-4-methyl-1H-benzoimidazol-2-yl)-4-methyl-pyrimidin-2-yl]-[3-(1-methyl-piperidin-4-y)-propyl]-amine) or a pharmaceutically acceptable salt, or a pharmaceutically acceptable prodrug, or a pharmaceutically active metabolite thereof; comprising

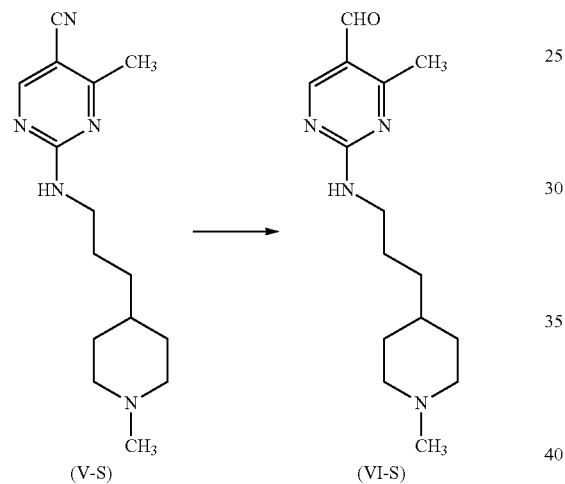

reacting a compound of formula (V-S) with a reducing agent system; in a solvent; at a temperature in the range of from about 0° C. to about 25° C., to yield compound of formula (VI-S); and

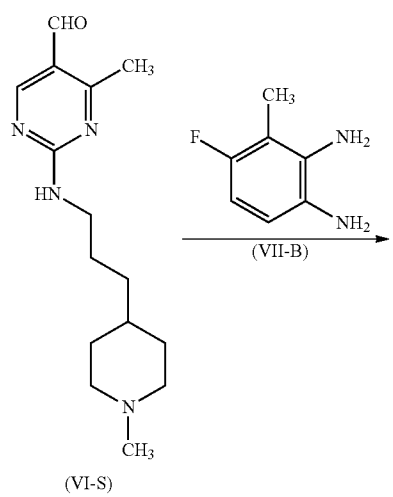

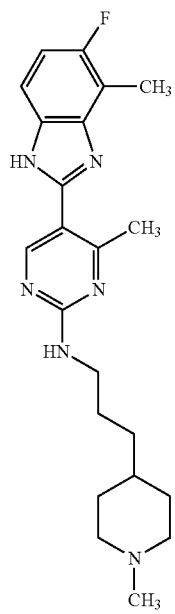

(I-B)

reacting compound of formula (VI-S) with a compound of formula (VII-B); in the presence of a suitably selected oxidizing agent or oxidizing agent system, in water or in an organic solvent, at a temperature in the range of from about 25° C. to about 100° C., to yield compound of formula (I-B).

The present invention is directed to a product prepared according to any of the processes described herein. The present invention is further directed to a crystalline hemi-tartrate of compound of formula (I-A). The present invention is further directed to a process for the preparation of a hemi-tartrate of compound of formula (I-A). The present invention is further directed to a process for the recrystallization of the hemi-tartrate of compound of formula (I-A).

In a further general aspect, the invention relates to pharmaceutical compositions each comprising: (a) an effective amount of at least one agent selected from compounds of Formula (I), prepared according to the process as described herein; and pharmaceutically acceptable salts, pharmaceutically acceptable prodrugs, and pharmaceutically active metabolites thereof; and (b) a pharmaceutically acceptable excipient.

In another general aspect, the invention is directed to a method of treating a subject suffering from or diagnosed with a disease, disorder, or medical condition mediated by histamine $H_4$ receptor activity, comprising administering to the subject in need of such treatment an effective amount of at least one compound of Formula (I), or a pharmaceutically acceptable salt, pharmaceutically acceptable prodrug, or pharmaceutically active metabolite of such compound, wherein compound of formula (I), pharmaceutically acceptable salt, prodrug or metabolite thereof is prepared according to the process as described herein. In certain embodiments of the inventive method, the disease, disorder, or medical condition is inflammation. Inflammation herein refers to the response that develops as a consequence of histamine release, which in turn is caused by at least one stimulus. Examples of such stimuli are immunological stimuli and non-immunological stimuli.

In another general aspect, the invention is directed to a method for modulating histamine $H_4$ receptor activity, comprising exposing histamine $H_4$ receptor to an effective amount of at least one of a compound of Formula (I) and a pharmaceutically acceptable salt, prodrug or metabolite thereof; wherein compound of formula (I), pharmaceutically acceptable salt, prodrug or metabolite thereof is prepared according to the process as described herein.

Additional embodiments, features, and advantages of the invention will be apparent from the following detailed description and through practice of the invention.

BRIEF DESCRIPTION OF THE FIGURES

FIG. 1 illustrates a powder X-ray diffraction (XRD) pattern for a crystalline hemi-tartrate of compound of formula (I-A).

DETAILED DESCRIPTION OF THE INVENTION

The present invention is directed to a process for the preparation of compound of formula (I)

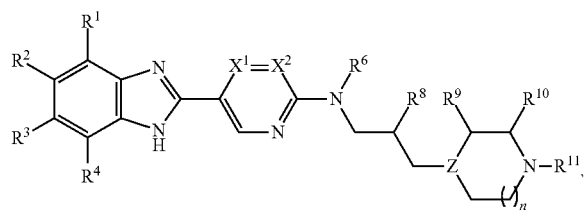

(I)

wherein $R^1$, $R^2$, $R^3$, $R^4$, $X^1$, $X^2$, $R^6$, $R^8$, Z, n, $R^9$, $R^{10}$ and $R^{11}$ are as herein defined. Embodiments of compounds of the present invention are useful as histamine $H_4$ receptor modulators.

In an embodiment of the present invention, compound of formula (I) is selected from the group consisting of a compound of formula (I-A)

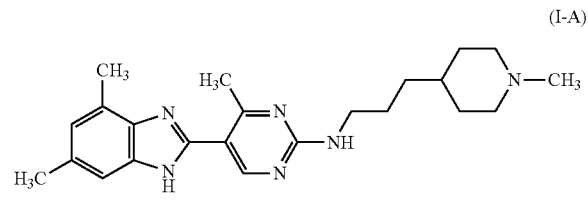

(I-A)

and pharmaceutically acceptable salts thereof; and a compound of formula (I-B)

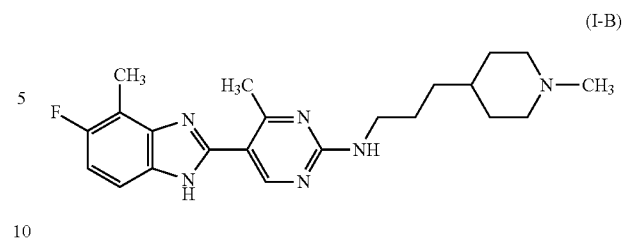

(I-B)

and pharmaceutically acceptable salts thereof.

In some embodiments of compounds of Formula (I), each of $R^{1-4}$ is independently H, methyl, tert-butyl, methoxy, —$CF_3$, —CN, fluoro, chloro, methoxycarbonyl, or benzoyl. In some embodiments, $X^2$ is N. In other embodiments, $X^1$ is N. In some embodiments, $R^c$ is H, methyl, ethyl, $CF_3$, cyclopropyl, or cyclobutyl. In further embodiments, $R^c$ is H or methyl. In some embodiments, n is 1. In some embodiments, Z is N or CH. In further embodiments, Z is CH. In some embodiments, $R^6$ is H, methyl, ethyl, propyl, isopropyl, cyclopropyl, or cyclobutyl. In further embodiments, $R^6$ is H or methyl. In some embodiments, $R^8$ is H. In some embodiments, $R^9$ and $R^{10}$ are each independently H or methyl. In further embodiments, $R^9$ and $R^{10}$ are both H. In some embodiments, $R^{11}$ is H or methyl. In further embodiments, $R^{11}$ is methyl.

In an embodiment, the present invention is directed to a process for the preparation of compounds of formula (I)

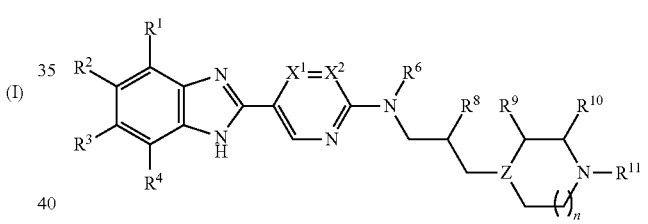

(I)

wherein $R^1$, $R^2$, $R^3$, $R^4$, $X^1$, $X^2$, $R^6$, $R^8$, $R^9$, $R^{10}$, $R^{11}$ and n are as herein defined; and pharmaceutically acceptable salts, pharmaceutically acceptable prodrugs, and pharmaceutically active metabolites thereof; comprising

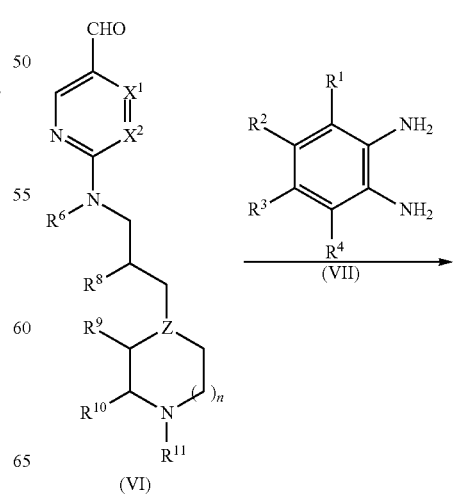

(VI)

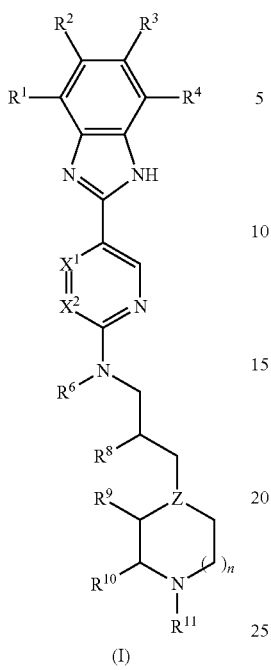

(I)

reacting a compound of formula (VI) with a compound of formula (VII); in the presence of a suitably selected oxidizing agent or oxidizing agent system, in water or in an organic solvent, at a temperature in the range of from about 25° C. to about 100° C.; to yield the compound of formula (I).

In another embodiment, the present invention is directed to a process for the preparation of a compound of formula (I-A)

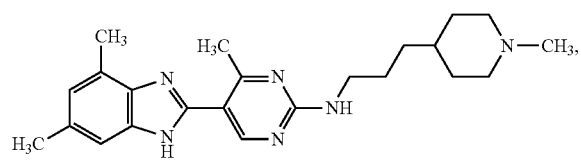

(I-A)

(also known as [5-(4,6-dimethyl-1H-benzoimidazol-2-yl)-4-methyl-pyrimidin-2-yl]-[3-(1-methyl-piperidin-4-yl)-propyl]-amine) or a pharmaceutically acceptable salt, or a pharmaceutically acceptable prodrug, or a pharmaceutically active metabolite thereof; comprising

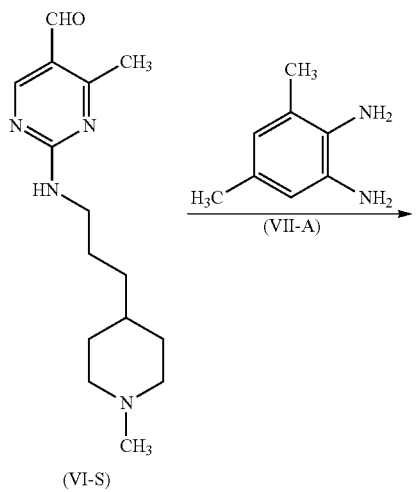

(VI-S)

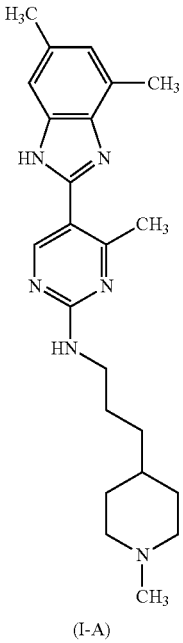

(I-A)

reacting a compound of formula (VI-S) with a compound of formula (VII-A); in the presence of a suitably selected oxidizing agent or oxidizing agent system, in water or in an organic solvent, at a temperature in the range of from about 25° C. to about 100° C., to yield compound of formula (I-A).

In yet another embodiment, the present invention is directed to a process for the preparation of a compound of formula (I-B)

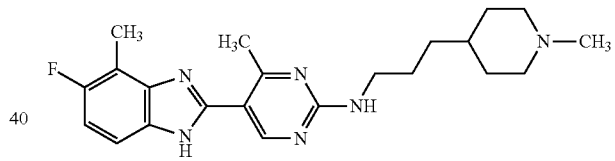

(I-B)

(also known as [5-(5-Fluoro-4-methyl-1H-benzoimidazol-2-yl)-4-methyl-pyrimidin-2-yl]-[3-(1-methyl-piperidin-4-yl)-propyl]-amine) or a pharmaceutically acceptable salt, or a pharmaceutically acceptable prodrug, or a pharmaceutically active metabolite thereof; comprising

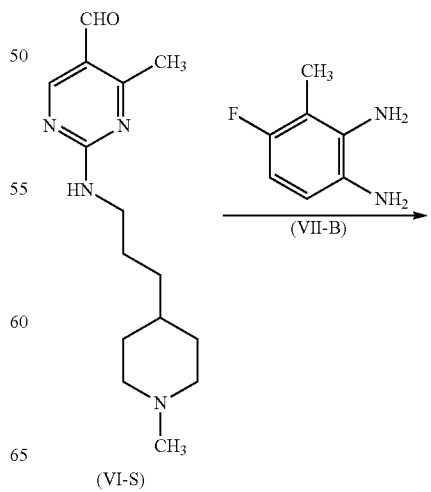

(VI-S)

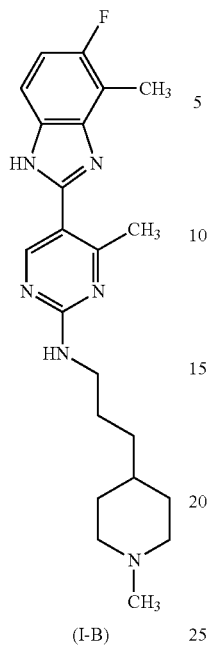

(I-B)

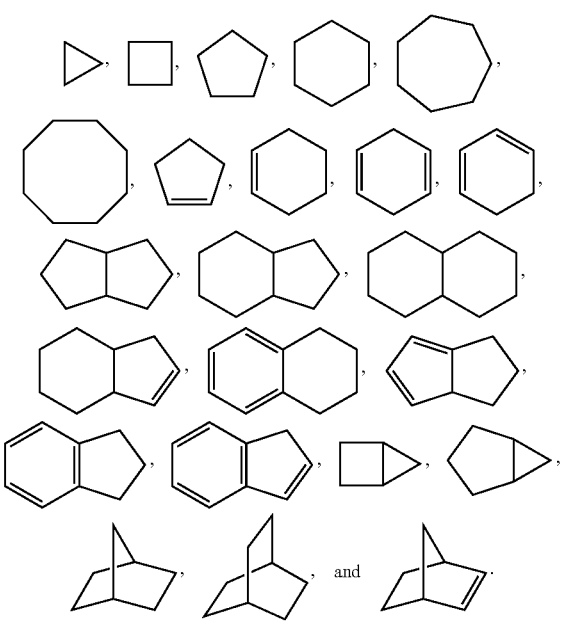

reacting a compound of formula (VI-S) with a compound of formula (VII-B); in the presence of a suitably selected oxidizing agent or oxidizing agent system, in water or in an organic solvent, at a temperature in the range of from about 25° C. to about 100° C., to yield compound of formula (I-B).

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The terms "halogen" and "halo" represents chlorine, fluorine, bromine, or iodine.

The term "alkyl" refers to a straight- or branched-chain alkyl group having from 1 to 12 carbon atoms in the chain. Examples of alkyl groups include methyl (Me, which also may be structurally depicted by the symbol "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkenyl" refers to a straight- or branched-chain alkenyl group having from 2 to 12 carbon atoms in the chain. (The double bond of the alkenyl group is formed by two $sp^2$ hybridized carbon atoms.) Illustrative alkenyl groups include prop-2-enyl, but-2-enyl, but-3-enyl, 2-methylprop-2-enyl, hex-2-enyl, and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

When a particular group is "substituted" (e.g., alkyl, cycloalkyl, aryl, heteroaryl, heterocycloalkyl, etc.), that group may have one or more substituents, for example, from one to five substituents, or from one to three substituents, or one to two substituents, independently selected from the list of substituents.

With reference to substituents, the term "independently" means that when more than one of such substituents is possible, such substituents may be the same or different from each other.

Any formula given herein is intended o represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof.

Furthermore, certain structures may exist as geometric isomers (i.e., cis and trans isomers), as tautomers, or as atropisomers. Additionally, any formula given herein is intended to represent hydrates, solvates, and polymorphs of such compounds, and mixtures thereof.

Reference to a chemical entity herein stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH$_{(s)}$, R—COOH$_{(sol)}$, and R—COO$^-$$_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-$$_{(sol)}$ refers to the dissociated form of the compound in a solvent, such as the dissociated form of the compound in an aqueous environment, whether such dissociated form derives from R—COOH, from a salt thereof, or from any other entity that yields R—COO⁻ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In this regard, if such entity is for example in an aqueous environment, it is understood that the compound R—COOH is in such same medium, and therefore the entity is being exposed to species such as R—COOH$_{(aq)}$ and/or R—COO⁻$_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. In another example, a zwitterionic compound is encompassed herein by referring to a compound that is known to form a zwitterions, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. (See, for example its on line version at http://www.ebi.ac.uk/chebi/init.do). As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula H$_2$NCH$_2$COOH, and it exists in some media (in this case in neutral media) in the form of the zwitterion ⁺H$_3$NCH$_2$COO⁻. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention when compounds referred to herein can form zwitterions. No further examples in this regard are provided herein because these interactions and transformations in a given medium are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Such isotopically labelled compounds are useful in metabolic studies (for example with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent S$^1_{example}$ is one of S$_1$ and S$_2$, and substituent S$^2_{example}$ is one of S$_3$ and S$_4$, then these assignments refer to embodiments of this invention given according to the choices S$^1_{example}$ is S$_1$ and S$^2_{example}$ is S$_3$; S$^1_{example}$ is S$_1$ and S$^2_{example}$ is S$_4$; S$^1_{example}$ is S$_2$ and S$^2_{example}$ is S$^1_{example}$ is S$_2$ and S$^2_{example}$ is S$_4$; and equivalents of each one of such choices. The shorter terminology "S$^1_{example}$ is one of S$_1$ and S$_2$, and S$^2_{example}$ is one of S$_3$ and S$_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as R$^{1-11}$, X$^1$, X$^2$, and n, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent S$_{example}$ is one of S$_1$, S$_2$, and S$_3$, this listing refers to embodiments of this invention for which S$_{example}$ is S$_1$; S$_{example}$ is S$_2$; S$_{example}$ is S$_3$; S$_{example}$ is one of S$_1$ and S$_2$; S$_{example}$ is one of S$_1$ and S$_3$; S$_{example}$ is one of S$_2$ and S$_3$; S$_{example}$ is one of S$_1$, S$_2$ and S$_3$; and S$_{example}$ is any equivalent of each one of these choices. The shorter terminology "S$_{example}$ is one of S$_1$, S$_2$, and S$_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as R$^{1-11}$, X$^1$, X$^2$, and n, and any other generic substituent symbol used herein.

The nomenclature "C$_{i-j}$" with j>i, when applied herein to a class of substituents, is meant to refer to embodiments of this invention for which each and every one of the number of carbon members, from i to j including i and j, is independently realized. By way of example, the term C$_{1-3}$ refers independently to embodiments that have one carbon member (C$_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n.

Any disubstituent referred to herein is meant to encompass the various attachment possibilities when more than one of such possibilities are allowed. For example, reference to disubstituent -A-B-, where A≠B. refers herein to such disubstituent with A attached to a first substituted member and B attached to a second substituted member, and it also refers to such disubstituent with A attached to the second substituted member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

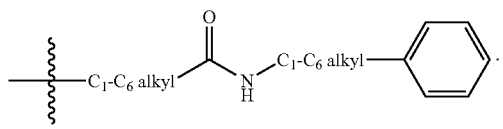

Abbreviations used in the specification, particularly the Schemes and Examples, are as follows:
DDQ=2,3-Dichloro-5,6-dicyanobenzoquinone
Dibal-H, DIBAL-H=Diisobutylaluminum hydride
DMA=Dimethylacetamide
DME=1,2-Dimethoxyethane
DMF=N,N-Dimethylformamide
EtOH=Ethanol
HPLC=High Pressure Liquid Chromatography
IPA=Isopropyl alcohol
2-Me-THF=Z-Methyl-tetrahydrofuran
MTBE=Methyl-t-butyl ether
NMM=N-Methylmorpholine
NMP=1-Methyl-2-pyrrolidinone
OXONE®=Potassium monopersulphate triple salt
RANEY® Nickel=Aluminum-nickel alloy
Red-Al=Sodium bis(2-methoxyethoxy)aluminum hydride
TEA=Triethylamine
TEMPO®=[2,2,6,6-tetramethyl-1-piperidinyloxy free radical]
THF=Tetrahydrofuran)
XRD=X-Ray Diffraction As used herein, unless otherwise noted, the term "isolated form" shall mean that the compound is present in a form which is separate from any solid mixture with another compound(s), solvent system or biological environment. In an embodiment of the present invention, compound of formula (I) is prepared as an isolated form. In another embodiment of the present invention, compound of formula (I-A) is prepared as an isolated form. In another embodiment of the present invention, compound of formula (I.B) is prepared as an isolated form.

As used herein, unless otherwise noted, the term "substantially pure" shall mean that the mole percent of impurities in the isolated compound is less than about 5 mole percent, for example, at less than about 2 mole percent. In an embodiment, the mole percent of impurities is less than about 0.5 mole percent, for example, less than about 0.1 mole percent. In an embodiment of the present invention, compound of formula (I) is prepared as a substantially pure compound. In another embodiment of the present invention, compound of formula (I-A) is prepared a substantially pure compound. In another embodiment of the present invention, compound of formula (I-B) is prepared a substantially pure compound.

As used herein, unless otherwise noted, the term "substantially free of a corresponding salt(s)" when used to described compound of formula (I) shall mean that mole percent of the corresponding salt form(s) in the isolated base of formula (I) is less than about 5 mole percent, for example, less than about 2 mole percent. In an embodiment, the mole percent of the corresponding salt form(s) is less than about 0.5 mole percent, for example, less than about 0.1 mole percent. In an embodiment of the present invention, compound of formula (I) is prepared in a form which is substantially free of corresponding salt. In another embodiment of the present invention, compound of formula (I-A) is prepared in a form which is substantially free of corresponding salt. In another embodiment of the present invention, compound of formula (I-B) is prepared in a form which is substantially free of corresponding salt.

The invention includes also pharmaceutically acceptable salts of the compounds represented by Formula (I), for example those described above and of the specific compounds exemplified herein.

A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as pyrrolidines, piperidine, morpholine, and piperazine, and inorganic salts derived from sodium, calcium, potassium, magnesium, manganese, iron, copper, zinc, aluminum, and lithium.

The invention also relates to treatment methods employing pharmaceutically acceptable prodrugs of compounds of Formula (I). The term "prodrug" means a precursor of a designated compound that, following administration to a subject, yields the compound in vivo via a chemical or physiological process such as solvolysis or enzymatic cleavage, or under physiological conditions (e,g., a prodrug on being brought to physiological pH is converted to compound of Formula (I)). A "pharmaceutically acceptable prodrug" is a prodrug that is not toxic, biologically intolerable, or otherwise biologically unsuitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl)amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl ($C_{1-6}$alkyl)esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115, Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

Pharmaceutically active metabolites may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J. Med. Chem.* 1997, 40, 2011-2016; Shan, et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites (collectively, "agents") of the present invention are useful as histamine $H_4$ receptor modulators in the methods of the invention. The agents may be used in the inventive methods for the treatment or prevention of medical conditions, diseases, or disorders mediated through modulation of the histamine $H_4$ receptor, such as those described herein. Agents according to the invention may therefore be used as an anti-inflammatory agents. Symptoms or disease states are intended to be included within the scope of "medical conditions, disorders, or diseases."

Accordingly, the invention relates to methods of using the pharmaceutical agents described herein to treat subjects diagnosed with or suffering from a disease, disorder, or condition mediated through histamine $H_4$ receptor activity, such as inflammation.

In another embodiment, an agent of the present invention is administered to treat inflammation. Inflammation may be associated with various diseases, disorders, or conditions, such as inflammatory disorders, allergic disorders, dermatological disorders, autoimmune disease, lymphatic disorders, and immunodeficiency disorders, including the more specific conditions and diseases given below. Regarding the onset and evolution of inflammation, inflammatory diseases or inflammation-mediated diseases or conditions include, but are not limited to, acute inflammation, allergic inflammation, and chronic inflammation, Illustrative types of inflammation treatable with a histamine $H_4$ receptor-modulating agent according to the invention include inflammation due to or associated with any one of a plurality of conditions such as allergy, asthma, eosiophilic asthma, dry eye, chronic obstructive pulmonary disease (COPD), atherosclerosis, rheumatoid arthritis, multiple sclerosis, inflammatory bowel diseases (including colitis, Crohn's disease, and ulcerative colitis), autoimmune diseases, sepsis, pain, insect bites, itch (associated with conditions such as the following: atopic dermatitis eczema, urticaria (hives), psoriasis, oncological conditions such as T cell lymphoma, associated with the administration of drugs to treat parasitic or fungal infections (e.g., lice, scabies, swimmer's itch, jock itch, athlete's foot), hidradenitis suppurativa, malignancy/lymphoma (e.g., Hodgkin's disease), jaundice, polycythemia, punctate palmoplantar keratoderma, thyroid illness/hyperparathyroidism, diabetes, primary biliary cirrhosis, chicken pox, iron deficiency anemia, psychiatric diseases, medication-induced cholestasis; pregnancy-related cholestasis (e.g., obstetric cholestasis), pruritic urticaria papules and plaques of pregnancy, gestational phemphigoid; xerosis (dry skin), sunburn, dandruff, scab/scars, insect bites. poison ivy/oak, hemorrhoids, contact dermatitis, old-age associated itch, and associated with dialysis), psoriasis, pruritus, dermal inflammation, itchy skin, photodermatitis, atopic dermatitis/eczema, chronic dermatitis, urticaria (hives including chronic uticaria), ocular inflammation, conjunctivitis, choroidal neovascularization in age-related macular degeneration, age-related macular degeneration, vernal keratoconjuctivitis, nasal polyps, allergic rhinitis, nasal itch, scleroderma, cancer (e.g. melanoma, breast cancer and colorectal cancer), autoimmune thyroid diseases, diabetes, type 2 diabetes and related disorders (such as chronic renal failure and hepatic cholestasis), immune-mediated (also known as type 1) diabetes mellitus and lupus, which are characterized by excessive or prolonged inflammation at some stage of the disease.

Additional illustrative types of inflammation treatable with a histamine $H_4$ receptor-modulating agent according to the invention include autoimmune diseases that lead to inflammation include Myasthenia gravis, autoimmune neuropathies, such as Guillain-Barré, autoimmune uveitis, autoimmune hemolytic anemia, pernicious anemia, autoimmune thrombocytopenia, temporal arteritis, anti-phospholipid syndrome, vasculitides, such as Wegener's granulomatosis, Behcet's disease, dermatitis herpetiformis, pemphigus vulgaris, vitiligio, primary biliary cirrhosis, autoimmune hepatitis, autoimmune oophoritis and orchitis, autoimmune disease of the adrenal gland, polymyositis, dermatomyositis, spondyloarthropathies, such as ankylosing spondylitis, and Sjogren's syndrome.

The invention may also be suitable for the treatment of mood disorders (including but not limited to major depressive disorder, bipolar disorder, treatment resistant major depressive disorder and treatment resistant bipolar disorder), anxiety disorders (including but not limited to generalized anxiety disorder, social phobia, and post traumatic stress disorder). The invention may also may have utility in the treatment of nociceptive and/or neuropathic pain.

In another embodiment, an agent of the present invention is administered to treat allergy, asthma, autoimmune diseases, or pruritus, The term "treat" or "treating" as used herein is intended to refer to administration of an agent or composition of the invention to a subject for the purpose of effecting a therapeutic or prophylactic benefit through modulation of histamine $H_4$ receptor activity. Treating includes reversing, ameliorating, alleviating, inhibiting the progress of, lessening the severity of, or preventing a disease, disorder, or condition, or one or more symptoms of such disease, disorder or condition mediated through modulation of histamine $H_4$ receptor activity. The term "subject" refers to a mammalian patient in need of such treatment, such as a human, "Modulators" include both inhibitors and activators, where "inhibitors" refer to compounds that decrease, prevent, inactivate, desensitize or down-regulate histamine $H_4$ receptor expression or activity, and "activators" are compounds that increase, activate, facilitate, sensitize, or up-regulate histamine $H_4$ receptor expression or activity.

In treatment methods according to the invention, an effective amount of at least one pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An example of a dose is in the range of from about 0.01 to about 200 mg of agent per kg of subject's body weight per day, or any range therein; for example about 0.05 to 100 mg/kg/day, or any range therein; or for example, about 1 to 35 mg/kg/day, or any range therein; in single or divided dosage units (e.g., BID, TID, QID). For a 70-kg human, an illustrative range for a suitable dosage amount is from about 0.05 to about 7 g/day, or any range therein; for example about 0.1 to about 2.5 g/day, or any range therein; for example 0.2 to about 1.0 g/day, or any range therein.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the agents of the invention may be used in combination with additional active compounds in the treatment of the above conditions. The additional compounds may be coadministered separately with an agent of Formula (I) or included with such an agent as an additional active ingredient in a pharmaceutical composition according to the invention. In an illustrative embodiment, additional active compounds are those that are known or discovered to be effective in the treatment of conditions, disorders, or diseases mediated by histamine $H_4$ receptor activity, such as another histamine $H_4$ receptor modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the agent according to the invention.

When referring to modulating the target receptor, an "effective amount" means an amount sufficient to affect the activity of such receptor. Measuring the activity of the target receptor may be performed by routine analytical methods. Target receptor modulation is useful in a variety of settings, including assays.

The agents of the invention are used, alone or in combination with one or more other active ingredients, to formulate pharmaceutical compositions of the invention. A pharmaceutical composition of the invention comprises an effective amount of at least one pharmaceutical agent in accordance with the invention. A pharmaceutically acceptable excipient is part of some embodiments of pharmaceutical compositions according to this invention.

A "pharmaceutically acceptable excipient" refers to a substance that is not toxic, biologically tolerable, or otherwise biologically suitable for administration to a subject, such as an inert substance, added to a pharmacological composition or otherwise used as a vehicle, carrier, or diluent to facilitate administration of a pharmaceutical agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the pharmaceutical agents may be prepared using suitable pharmaceutical excipients and compounding techniques known or that become available to those of ordinary skill in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. In an example, the compositions are formulated for intravenous infusion, topical administration, or oral administration.

For oral administration, the compounds of the invention can be provided in the form of tablets or capsules, or as a solution, emulsion, or suspension. To prepare the oral compositions, the agents may be formulated to yield a dosage of, e.g., from about 0.01 to about 200 mg/kg daily, or any range therein; for example from about 0.05 to about 100 mg/kg daily, or any range therein; or for example from about 0.05 to about 50 mg/kg daily, or any range therein; or for example from about 0.05 to about 25 mg/kg/day, or any range therein; or for example, from about 0.1 to about 10 mg/kg/day, or any range therein.

Oral tablets may include the agent and any other active ingredients mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Examples of liquid oral excipients include ethanol, glycerol, water, and the like. Starch, polyvinyl-pyrrolidone (PVP), sodium starch glycolate, microcrystalline cellulose, and alginic acid are examples of disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent, admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Agents may alternatively be administered in methods of this invention by inhalation, via the nasal or oral routes, e.g., in a spray formulation also containing a suitable carrier.

Examples of agents useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I).

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One of ordinary skill in the art will recognize that, where not otherwise specified, the reaction step(s) is performed under suitable conditions, according to known methods, to provide the desired product. One of ordinary skill in the art will further recognize that, in the specification and claims as presented herein, wherein a reagent or reagent class/type (e.g., base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one of ordinary skill in the art will recognize that wherein a reaction step of the present invention may be carried out in a variety of solvents or solvent systems, said reaction step may also be carried out in a mixture of the suitable solvents or solvent systems.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

Examples of suitable solvents, bases, reaction temperatures, and other reaction parameters and components are provided in the detailed descriptions which follows herein. One of ordinary skill in the art will recognize that the listing of said examples is not intended, and should not be construed, as limiting in any way the invention set forth in the claims which follow thereafter.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene and acetone.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, cyano and triflate.

As used herein, unless otherwise noted, the term "nitrogen protecting group" shall mean a group which may be attached to a nitrogen atom to protect said nitrogen atom from participating in a reaction and which may be readily removed following the reaction. Illustrative suitable nitrogen protecting groups include, but are not limited to, carbamates (which are groups that contain a moiety —C(O)O—R, wherein R is for example methyl, ethyl, t-butyl, benzyl, phenylethyl, $CH_2$=CH—$CH_2$— and 2,2,2-trichloroethyl); amides (which are groups that contain a moiety —C(O)—R', wherein R' is for example methyl, phenyl, trifluoromethyl and t-butyl (pivalol)); N-sulfonyl derivatives (which are groups that contain a moiety —$SO_2$—R", wherein R" is for example methyl, tolyl, phenyl, trifluoromethyl, 2,2,5,7,8-pentamethylchroman-6-yl- and 2,3,6-trimethyl-4-methoxybenzene). Other suitable nitrogen protecting groups may be found in texts such as P. G. M. Wuts & T. W. Greene Protective Groups in Organic Synthesis, John Wiley & Sons, 2007, and Protective Groups in Organic Chemistry, ed. J. F. W. McOmie, Plenum Press, 1973.

One of ordinary skill in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and P. G. M. Wuts & T. W. Greene *Protective Groups in Organic Synthesis*, John Wiley & Sons, 2007. The protecting groups may be removed at a convenient subsequent stage using methods known from the art.

The present invention is directed to a process for the preparation of a compound of formula (I) as outlined in more detail in Scheme 1, below.

Scheme 1

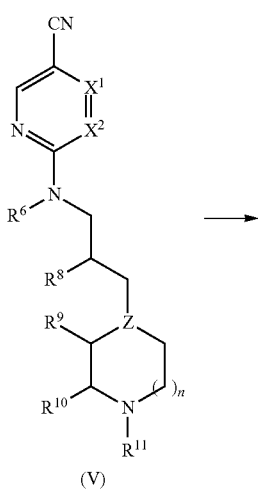

(V)

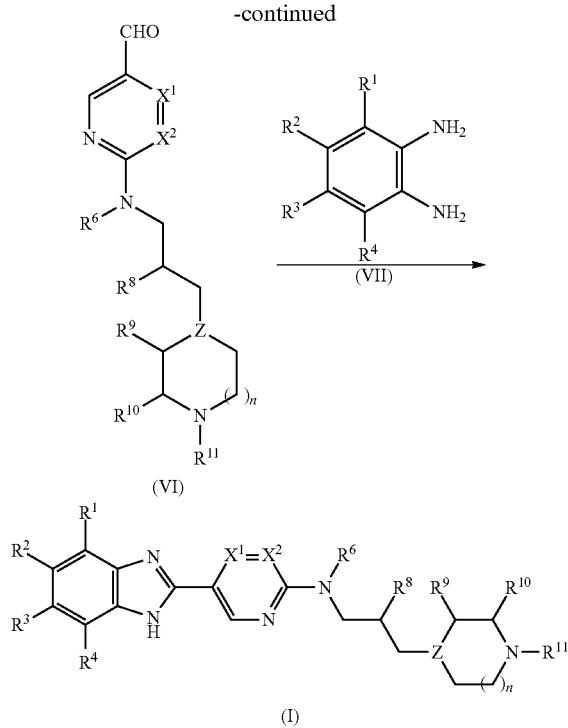

(I)

Referring to Scheme 1, a suitably substituted compound of formula (V), a known compound or compound prepared by known methods, is reacted with a suitably selected reducing agent system such as DIBAL-H, RANEY® nickel in the presence of a source of hydrogen such as $H_2(g)$, formic acid, and any other source of hydrogen that behaves like $H_2(g)$ and formic acid under these conditions, Red-Al, sodium borohydride, cupric hydride or lithium triethylborohydride, to yield compound of formula (VI). In some embodiments DIBAL-H or RANEY® nickel is used in the presence of a source of hydrogen. When the reducing agent system is a single agent, such as DIBAL-H, the reducing agent system is present in an amount in the range of from about 1.0 to about 5.0 molar equivalents (relative to the moles of compound of formula (V). In some embodiments, in an amount in the range of from about 2.0 to about 3.0 molar equivalents. In other embodiments, at about 2.5 molar equivalent. In an another example, the reducing agent system is RANEY® RANEY nickel in the presence of a source of hydrogen and RANEY® nickel is present in an amount in the range of from about 1.0 to about 10.0 molar equivalents, for example at about 200% by weight. In another example, the source of hydrogen is formic acid, and the formic acid is present in excess amount, for example at about 40 molar equivalents.

Examples of suitable solvents include the following. Where the reducing agent system is DIBAL-H, the reduction can be performed in an organic solvent, such as THF, toluene, 2-Me-THF, DME or MTBE. Such organic solvent may be an anhydrous organic solvent, such as THF or toluene. In another example, the reducing agent system is RANEY® nickel and a source of hydrogen such as formic acid, in water. The reaction temperature is in the range of from about 0° C. to about 25° C. In some embodiments, where the reducing agent system is DIBAL-H, the temperature is from about 5° C. to about 10° C. In other embodiments, where the reducing agent system is RANEY® nickel and a source of hydrogen such as formic acid, the temperature is about room temperature.

Compound of formula (VI) is reacted with a suitably substituted compound of formula (VII) to yield compound of formula (I), such compound of formula (VII) being present as a free base or as its corresponding salt form, a known compound or compound prepared by known methods. Compound of formula (VII) is present in an amount in the range of from about 1.0 to about 1.25 molar equivalents, for example in an amount in the range of from about 1.0 to about 1.1 molar equivalents, for example at about 1.01 molar equivalents. This reaction is performed in the presence of a suitably selected oxidizing agent or oxidizing agent system, such as $Na_2SO_3$/air, $Na_2S_2O_5$/air, $NaHSO_3$/air, DDQ, OXONE® or TEMPO® in combination with sodium hypochlorite, for example $Na_2SO_3$/air or $Na_2S_2O_5$/air. The term "oxidizing agent system" is herein used to generically refer to any such oxidizing agent or oxidizing agent system. Such oxidizing agent or oxidizing agent system is present in an amount in the range of from about 0.90 to about 1.5 molar equivalents, for example in an amount in the range of from about 0.95 to about 1.3 molar equivalents, for example in an amount of about 1.3 molar equivalents, and still in another example in an amount of about 1.0 molar equivalents. This reaction's medium is water in some embodiments or an organic solvent in other embodiments. Examples of such organic solvents include DMF, NMP, DMA, acetonitrile and ethanol. Some reaction media are DMF, and in other examples, they are water. This reaction is performed at a temperature in the range of from about 25° C. to about 100° C., for example at a temperature in the range of from about 55° C. to about 65° C.

One of ordinary skill in the art will recognize that when compound of formula (VI) is reacted with compound of formula (VII) as its corresponding salt form in an organic solvent, then the reaction is run in the presence of a suitably selected organic or inorganic base such as such as NMM, TEA or $K_2CO_3$, for example $K_2CO_3$. One of ordinary skill in the art will further recognize that the base is present to neutralize the salt form of compound of formula (VII) and thereby liberate the diamine compound of formula (VII). One of ordinary skill in the art will further recognize that compound of formula (VI) may alternatively be reacted with compound of formula (VII) as its corresponding salt form in water, in the presence of a suitably selected acid such as HCl, $H_2SO_4$, and any other acid that behaves like any of these acids in the present reaction conditions.

In an embodiment, the present invention is directed to a process for the preparation of a compound of formula (I-A), as outlined in more detail in Scheme 2, below.

Scheme 2

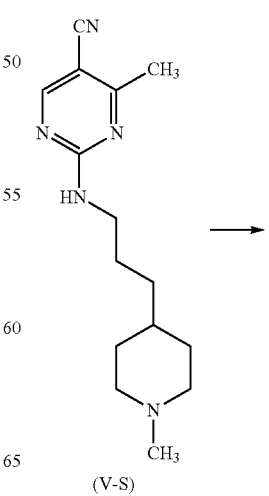

(V-S)

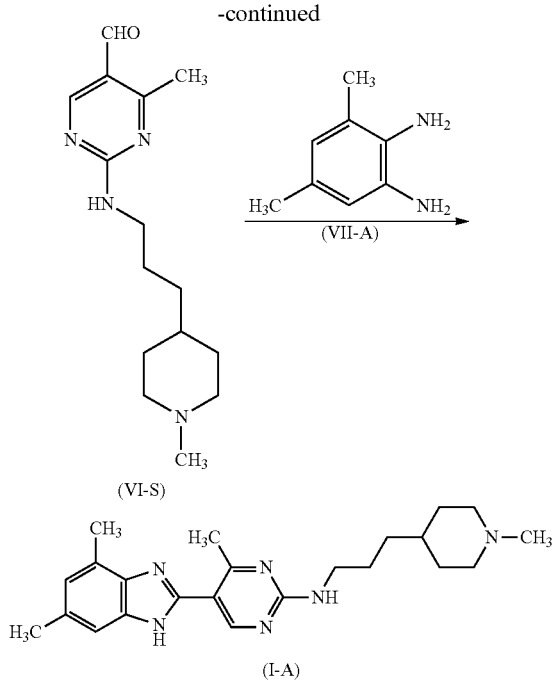

Referring to Scheme 2, a suitably substituted compound of formula (V-S), a known compound or compound prepared by known methods, is reacted with a suitably selected reducing agent system to yield to yield compound of formula (VI-S). Examples of reducing agent systems include DIBAL-H, RANEY® nickel in the presence of a source of hydrogen such as $H_2(g)$, formic acid, and any other hydrogen source that behaves under these conditions like hydrogen gas and formic acid, Red-Al, sodium borohydride, cupric hydride or lithium triethylborohydride. In some embodiments, the reducing agent system is DIBAL-H or RANEY® nickel in the presence of a source of hydrogen.

Where the reducing agent system is a single agent such as DIBAL-H, the reducing agent system is present in an amount in the range of from about 1.0 to about 5.0 molar equivalents (relative to the moles of compound of formula (V-S). In other embodiments, in an amount in the range of from about 2.0 to about 3.0 molar equivalents. Still in other embodiments at about 2.5 molar equivalent.

In other embodiments, the reducing agent system is RANEY® nickel in the presence of a source of hydrogen and RANEY® nickel is present in an amount in the range of from about 1.0 to about 10.0 molar equivalents, for example at about 200% by weight. In other embodiments, the source of hydrogen is formic acid, and the formic acid is present in excess amount, for example at about 40 molar equivalents.

Examples of solvents for this reaction include the following. The reducing agent system DIBAL-H is used in an organic solvent, such as THF, toluene, 2-Me-THF, DME and MTBE. In some embodiments, the organic solvent is an anhydrous organic solvent, for example in THF or toluene. The reducing agent system RANEY® nickel and a source of hydrogen, such as formic acid, the solvent is water. The temperature is in the range of from about 0° C. to about 25° C. When the reducing agent system is DIBAL-H, then the temperature is from about 5 to about 10° C. In another example, where the reducing agent system is RANEY® nickel and a source of hydrogen, such as formic acid, the reaction is performed at about room temperature.

Compound of formula (VI-S) is reacted with a suitably substituted compound of formula (VII-A), to yield compound of formula (I-A), wherein compound of formula (VII-A) may be present as a free base or as its corresponding salt form, a known compound or compound prepared by known methods. Compound of formula (VII-A) is present in an amount in the range of from about 1.0 to about 1.25 molar equivalents. In some embodiments, it is present in an amount in the range of from about 1.0 to about 1.1 molar equivalents. In still other embodiments, at about 1.01 molar equivalents. This reaction is performed in the presence of a suitably selected oxidizing agent or oxidizing agent system, such as $Na_2SO_3$/air, $Na_2S_2O_5$/air, $NaHSO_3$/airDDQ, OXONE® or TEMPO® in combination with sodium hypochlorite. In some embodiments, this oxidizing agent system is $Na_2SO_3$/air or $Na_2S_2O_5$/air. The oxidizing agent or oxidizing agent system is present in an amount in the range of from about 0.90 to about 1.5 molar equivalents. In some embodiments, in an amount in the range of from about 0.95 to about 1.3 molar equivalents. In other embodiments, in an amount of about 1.3 molar equivalents, and still in other embodiments in an amount of about 1.0 molar equivalents. The medium for this reaction is water or an organic solvent such as DMF, NMP, DMA, acetonitrile and ethanol. In some embodiments, the medium is DMF, and in other examples, it is water. The reaction temperature is in the range of from about 25° C. to about 100° C. In some embodiments, the temperature is in the range of from about 55° C. to about 65° C.

One of ordinary skill in the art will recognize that when compound of formula (VI-S) is reacted with compound of formula (VII-A) as its corresponding salt form in an organic solvent, then the reaction is run in the presence of a suitably selected organic or inorganic base such as such as NMM, TEA or $K_2CO_3$, for example $K_2CO_3$. One of ordinary skill in the art will further recognize that the base is present to neutralize the salt form of compound of formula (VII-A) and thereby liberate the diamine compound of formula (VII-A). One of ordinary skill in the art will further recognize that compound of formula (VI-S) may alternatively be reacted with compound of formula (VII-A) as its corresponding salt form in water, in the presence of a suitably selected acid such as HCl, $H_2SO_4$, and any other acid that behaves like hydrochloric and sulfuric acids in these conditions.

In an embodiment, the present invention is directed to a process for the preparation of a compound of formula (I-B), as outlined in more detail in Scheme 3, below.

Scheme 3

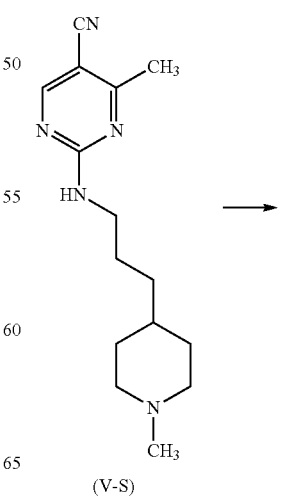

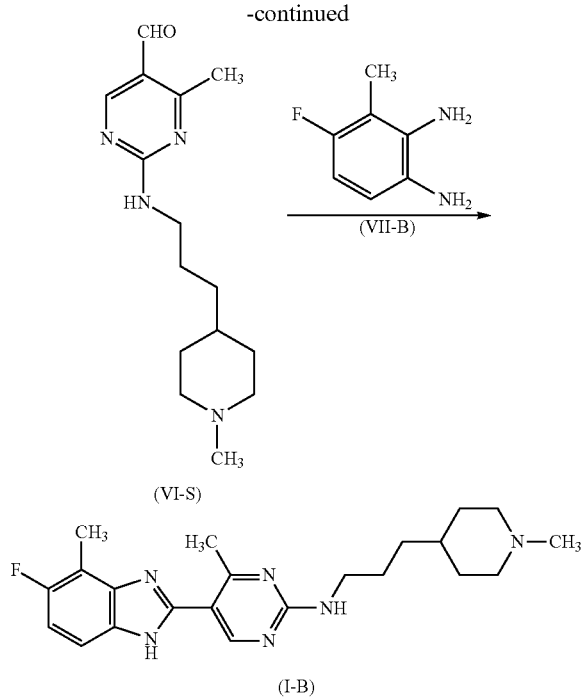

With reference to Scheme 3, a suitably substituted compound of formula (V-S), a known compound or compound prepared by known methods, is reacted with a suitably selected reducing agent system such as Dibal-H, RANEY® nickel in the presence of a source of hydrogen such as H$_2$(g), formic acid, and any other hydrogen source that behaves under these conditions as hydrogen gas and formic acid do. Red-Al, sodium borohydride, cupric hydride or lithium triethylborohydride, to yield the compound of formula VI-S), In some embodiments, the reducing agent system is Dibal-H or RANEY® nickel in the presence of a source of hydrogen, In an embodiment, where the reducing agent system is a single agent, such as DIBAL-H, the reducing agent system is present in an amount in the range of from about 1.0 to about 5.0 molar equivalents (relative to the moles of compound of formula (V-S). In another embodiment, in an amount in the range of from about 2.0 to about 3.0 molar equivalents, and still in other embodiments, in an amount of about 2.5 molar equivalent.

Where the reducing agent system is RANEY® nickel in the presence of a source of hydrogen, RANEY® nickel is present in an amount in the range of from about 1.0 to about 10.0 molar equivalents, for example at about 200% by weight. Where the source of hydrogen is formic acid, it is present in an excess amount, for example about 40 molar equivalents of formic acid, Examples of solvents for this reaction are the following Where the reducing agent system is DIBAL-H, the solvent is an organic solvent, such as THF, toluene, 2-Me-THF, DME and MTBE. Such organic solvent may in some embodiments be an anhydrous organic solvent, for example THF or toluene. Where the reducing agent system is RANEY® nickel and the source of hydrogen is formic acid, the solvent is typically water.

The reaction temperature is in the range of from about 0° C. to about 25° C. In some embodiments, where the reducing agent system is DIBAL-H, the temperature is from about 5° C. to about 10° C. In other embodiments, where the reducing agent system is RANEY® nickel with a source of hydrogen such as formic acid, the temperature is about room temperature.

Compound of formula (VI-S) is reacted with a suitably substituted compound of formula (VII-B), wherein compound of formula (VII-B) may be present as a free base or as its corresponding salt form, a known compound or compound prepared by known methods, to yield the compound of formula (I-B). Compound of formula (VII-B) is present in an amount in the range of from about 1.0 to about 1.25 molar equivalents. In some embodiments, the compound of formula (VII-B) is present in an amount in the range of from about 1.0 to about 1.1 molar equivalents. In other embodiments, the compound of formula (VII-B) is present in an amount of about 1.01 molar equivalents. This reaction takes place in the presence of a suitably selected oxidizing agent or oxidizing agent system, such as Na$_2$SO$_3$/air, Na$_2$SO$_5$/air, NaHSO$_3$/air, DDQ, OXONE® or TEMPO® in combination with sodium hypochlorite. In some embodiments, Na$_2$SO$_3$/air or Na$_2$S$_2$O$_5$/air is used. The oxidizing agent or oxidizing agent system is present in an amount in the range of from about 0.90 to about 1.5 molar equivalents. In some embodiments, the oxidizing agent or oxidizing agent system is present in an amount in the range of from about 0.95 to about 1.3 molar equivalents. In other embodiments, the oxidizing agent or oxidizing agent system is present in an amount of about 1.3 molar equivalents, and still in other embodiments, in an amount of about 1.0 molar equivalents. This reaction takes place in water or in an organic solvent such as DMF, NMP, DMA, acetonitrile or ethanol. In some embodiments, the reaction medium is provided by DMF. The reaction temperature is in the range of from about 25° C. to about 100° C. In other embodiments the reaction temperature is in the range of from about 55 to about 65° C.

One of ordinary skill in the art will recognize that when compound of formula (VI-S) is reacted with a salt form of compound of formula (VII-B) in an organic solvent, then the reaction is run in the presence of a suitably selected organic or inorganic base such as NMM, TEA and K$_2$CO$_3$. In some embodiments, K$_2$CO$_3$ is used as such base. One of ordinary skill in the art will further recognize that the base is present to neutralize the salt form of compound of formula (VII-B) and thereby liberate the diamine compound of formula (VII-B). One of ordinary skill in the art will further recognize that compound of formula (VI-S) may alternatively be reacted with compound of formula (VII-B) as its corresponding salt form in water, in the presence of a suitably selected acid such as HCl, H$_2$SO$_4$, and other acids that behave like hydrochloric and sulfuric acids in these conditions.

Powder X-ray diffraction patterns listed herein were measured using an XPERT-PRO diffractometer system. The sample was backloaded into a conventional x-ray holder and tested at 25° C. The sample was scanned from 4.01°2θ to 40.98°2θ with a step size of 0.0170°2θ and a time per step of 17.44 seconds. Instrument voltage and current settings were 45 kV and 40 mA.

The present invention is further directed to a crystalline hemi-tartrate of compound of formula (I-A). The crystalline hemi-tartrate of compound of formula (I-A) may be characterized, for example, by its powder XRD pattern, an example of which is shown in FIG. 1 herein.

In an embodiment, the crystalline hemi-tartrate of compound of formula (I-A) may be characterized by its powder X-ray diffraction pattern comprising the peaks as listed in Table 1, below.

TABLE 1

XRD Peaks

| Pos. [°2θ] | FWHM [°2θ] | d-spacing [Å] | Rel. Int. [%] |
|---|---|---|---|
| 6.49 | 0.15 | 13.62 | 100 |
| 8.58 | 0.17 | 10.30 | 48 |
| 9.17 | 0.20 | 9.64 | 5 |
| 10.35 | 0.13 | 8.55 | 10 |
| 10.75 | 0.20 | 8.23 | 23 |
| 12.92 | 0.20 | 6.85 | 4 |
| 15.37 | 0.40 | 5.77 | 1 |
| 16.72 | 0.40 | 5.30 | 6 |
| 17.46 | 0.20 | 5.08 | 6 |
| 18.89 | 0.17 | 4.70 | 9 |
| 20.72 | 0.54 | 4.29 | 2 |
| 22.14 | 0.40 | 4.02 | 4 |
| 23.60 | 0.22 | 3.77 | 24 |
| 25.92 | 0.80 | 3.44 | 2 |
| 28.09 | 0.54 | 3.18 | 1 |
| 29.88 | 0.27 | 2.99 | 1 |
| 35.53 | 0.80 | 2.53 | 0.2 |

In an embodiment of the present invention, the crystalline hemi-tartrate of compound of formula (I-A) is characterized by its powder XRD pattern which comprises peaks having a relative intensity greater than or equal to about 5%, as listed in Table 2 below.

TABLE 2

XRD Peaks

| Pos. [°2θ] | FWHM [°2θ] | d-spacing [Å] | Rel. Int. [%] |
|---|---|---|---|
| 6.49 | 0.15 | 13.62 | 100 |
| 8.58 | 0.17 | 10.30 | 48 |
| 9.17 | 0.20 | 9.64 | 5 |
| 10.35 | 0.13 | 8.55 | 10 |
| 10.75 | 0.20 | 8.23 | 23 |
| 16.72 | 0.40 | 5.30 | 6 |
| 17.46 | 0.20 | 5.08 | 6 |
| 18.89 | 0.17 | 4.70 | 9 |
| 23.60 | 0.22 | 3.77 | 24 |

In an embodiment of the present invention, the crystalline hemi-tartrate of compound of formula (I-A) is characterized by its powder XRD pattern which comprises peaks having a relative intensity greater than or equal to about 10%, as listed in Table 3 below.

TABLE 3

XRD Peaks

| Pos. [°2θ] | FWHM [°2θ] | d-spacing [Å] | Rel. Int. [%] |
|---|---|---|---|
| 6.49 | 0.15 | 13.62 | 100 |
| 8.58 | 0.17 | 10.30 | 48 |
| 10.35 | 0.13 | 8.55 | 10 |
| 10.75 | 0.20 | 8.23 | 23 |
| 23.60 | 0.22 | 3.77 | 24 |

In an embodiment of the present invention, the crystalline hemi-tartrate of compound of formula (I-A) is characterized by its powder XRD pattern which comprises peaks having a relative intensity greater than or equal to about 20%, as listed in Table 4, below.

TABLE 4

XRD Peaks

| Pos. [°2θ] | FWHM [°2θ] | d-spacing [Å] | Rel. Int. [%] |
|---|---|---|---|
| 6.49 | 0.15 | 13.62 | 100 |
| 8.58 | 0.17 | 10.30 | 48 |
| 10.75 | 0.20 | 8.23 | 23 |
| 23.60 | 0.22 | 3.77 | 24 |

The present invention is further directed to a process for the preparation of a hemi-tartrate of compound of formula (I-A). The hemi-tartrate of compound of formula (I-A) may be prepared according to the following process.

Compound of formula (I-A) is dissolved in an organic solvent such as denatured ethanol, methanol or IPA. In some embodiments, denatured ethanol is used. In other embodiments, a mixture of denatured ethanol and isopropanol is used.

Water is optionally removed from the compound of formula (I-A) solution. In some embodiments, water is removed azeotropically. In some embodiments, water is removed azeotropically by adding a suitably selected organic solvent, such as cyclohexane, to the compound of formula (I-A) solution, and subjecting the resulting mixture to azeotropic distillation.

With or without water removal from it, the solution of compound of formula (I-A), is heated to a temperature in the range of from about 35° C. to about reflux, for example to a temperature of about 50° C., and L-tartaric acid is added to the heated mixture. L-tartaric acid is added in an amount in the range of from about 0.25 to about 1.0 molar equivalents. In some embodiments, L-tartaric acid is added in an amount of about 0.5 molar equivalents.

The mixture with the added L-tartaric acid is heated to a temperature in the range of from about 50° C. to about reflux. In some embodiments, the mixture with the added L-tartaric acid is heated to a temperature of about 50° C. In other embodiments, the mixture with the added L-tartaric acid is heated to a temperature from about 70° C. to about 75° C. The resulting mixture is optionally filtered. With or without filtration, a tartrate solution is obtained.

Embodiments of this invention optionally include one or more of the following additional steps to obtain the solid hemi tartrate compound of formula (I-A). In some embodiments, the tartrate solution is cooled at a temperature below room temperature. In other embodiments, the cooling is effectuated to a temperature of from about 0° C. to about −5° C. A precipitate of the hemi-tartrate of compound of formula (I-A) is obtained. In addition, this precipitate can be further isolated. Such isolation is achieved by washing the precipitate with cold organic solvent, and further optionally drying the precipitate according to known methods, for example under vacuum and/or under elevated temperature.

The present invention is further directed to a process for the recrystallization of the hemi-tartrate of compound of formula (I-A). In some embodiments, the recrystallization optionally may include one or more of the following additional steps. In some embodiments, the recrystallization is performed by dissolving the hemi-tartrate of compound of formula (I-A) in a mixture of water and an organic solvent, such as denatured ethanol, and optionally filtering the resultant mixture. Illustrative examples of such water/organic solvent mixture are given by an about 1% (vol/vol) water:denatured ethanol mixture; a mixture of water and denatured ethanol, wherein the water is present in from about 1.0% to about 1.5% by weight;

and a mixture of water and denatured ethanol, wherein the water is present in about 1.4% by weight. In some embodiments, removing water from the so-prepared mixture yields a mixture with boiling point of between about 70° C. and about 80° C. In some embodiments, such boiling point is between about 70° C. and about 75° C. In other embodiments, such boiling point is between about 78° C. and about 80° C. This water removal is accomplished in some embodiments by azeotropic distillation. The resulting mixture is subsequently optionally filtered.

Embodiments of this invention optionally include one or more of the following additional steps to obtain recrystallized compound of formula (I-A) hemi-tartrate. In some embodiments, the invention may include cooling the mixture to yield a precipitate of the crystalline hemi-tartrate of compound of formula (I-A). An example of such is, cooling to a temperature of about 0° C. and optionally subsequently isolating of the precipitate. An example of such isolation is by filtration, wherein the filtrate is optionally washed with cold organic solvent. The washed precipitate is optionally dried according to known methods, for example under vacuum and/or under elevated temperature.

In another aspect, the present invention is directed to a process for a subsequent recrystallization of the hemi-tartrate of compound of formula (I-A) as follows. In some embodiments, the recrystallization optionally may include one or more of the following additional steps. In some embodiments, the recrystallization includes dissolving the hemi-tartrate of compound of formula (I-A) in a mixture of organic solvents, such as a mixture of methanol and denatured ethanol. In some embodiments, the recrystallization includes optionally heating such mixture to a temperature greater than about room temperature. Examples of such temperature include about reflux temperature, and a temperature in the range of from about 50° C. to about 60° C. In some embodiments, the recrystallization includes subsequently, optionally filtering the resultant mixture.

The so-prepared mixture is subsequently cooled to yield a precipitate of the crystalline hemi-tartrate of compound of formula (I-A). In some embodiments, it is cooled to about 0° C. In some embodiments, such cooling is effectuated in a step-wise manner. The so-formed precipitate is subsequently isolated. In some embodiments, the isolation is effectuated by filtration, and the isolated precipitate is optionally washed with cold organic solvent. The precipitate is optionally dried according to known methods, for example under vacuum and/or under elevated temperature.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum or a syrup.

Example 1, STEPS A-D describe recipes/procedures for the synthesis of the title compounds. Several batches of said compounds were prepared according to the recipes procedures as described below. The physical properties (e.g., MS+, 1H NMR, etc.) listed at the end of the synthesis descriptions below are a listing of the physical properties measured for a representative sample of the prepared compound.

EXAMPLE 1

[5-(4,6-Dimethyl-1H-benzoimidazol-2-yl)-4-methyl-pyrimidin-2-yl]-[3-(1-methyl-piperidin-4-yl)-propyl]-amine

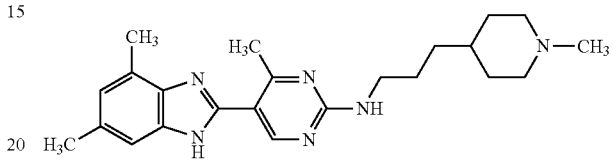

Step A

A 100 L glass-lined reactor was charged with 4-methyl-2-((3-(1-methylpiperidin-4-yl)propyl)amino)pyrimidine-5-carbonitrile (5.41 kg, 19.8 mol) and toluene (47.13 kg). The resultant suspension was stirred and cooled to about 0 to −5° C. Next, 1.0M diisobutylaluminum hydride (DIBAL-H) in toluene (40.55 kg, 47.33 mol) was added, via nitrogen pressure, while maintaining the internal reaction temperature at <2° C. After completing the addition, the resultant reaction solution was warmed to about 5-10° C. and the reaction monitored for completion by HPLC. Cold ethyl acetate (4.89 kg) was then added over 30 min and the resultant mixture stirred for 15-20 minutes. The resultant mixture (containing 4-methyl-2-((3-(1-methylpiperidin-4-yl)propyl)amino)pyrimidine-5-carbaldehyde) was transferred to a 100 L glass receiver and rinsed with toluene (1.00 kg).

Step B

A cold solution of water/sulfuric acid (27.05 kg/2.26 kg) to each, a 100 L Hastelloy reactor and a 100 L glass lined reactor. The resultant aqueous acid solutions were stirred and cooled to about 2-5° C. Maintaining the temperature <30° C. at all times, 50% (by volume) of the mixture prepared in STEP A above was added to each aqueous sulfuric acid solution. The resultant suspension was checked for pH (target pH of 4-5) and stirred at about 20-25° C. for about 1.5-2 h. The suspensions were then cooled to about 10-15° C. and the pH of the suspensions adjusted to pH~11-12, by adding 6N sodium hydroxide (16.12 kg, 81.42 mol), over 20 min. The resultant mixtures were then stirred to an additional 15-20 minutes, the agitation was then stopped and the phases allowed to separate.

The organic phases were removed from the top of each reactor via vacuum and combined. Then the aqueous phase and middle oil phases were drained via the bottom valve of each reactor and discarded. The combined organic phase was concentrated at ~40° C. to yield a solid. This solid was transferred to drying trays and dried (60 Torr, 30-35° C.) overnight to yield solid 4-methyl-2-((3-(1-methylpiperidin-4-yl)propyl)amino)pyrimidine-5-carbaldehyde.

Step C

In a 100 L glass-lined reactor, sodium metabisulfite ($Na_2S_2O_5$) (1.96 kg, 9.79 mol) was dissolved in purified water (54.63 kg), followed by the addition of 3,5-dimethyl-1,2-benzenediamine-2HCl (2.07 kg, 9.86 mol) and the resultant mixture stirred at about 20-25° C. to effect solution. Next, concentrated hydrochloric acid (1.65 kg, 16.79 mol) was added, followed by addition of 4-methyl-2-((3-(1-methylpiperidin-4-yl)propyl)amino)pyrimidine-5-carbaldehyde, prepared as in STEP B above (2.74 kg, 9.79 mol) and the resultant mixture stirred at about 23-27° C. to effect solution. The resultant mixture was heated to about 57-62° C. and monitored for completion by HPLC.

The reaction mixture was cooled to about 20-25° C. and then half of the volume (~30 L) was then added, via a metering pump, to a stirring 50 L glass reactor system containing a solution of potassium carbonate (3.9 kg, 28.2 mol) dissolved in purified water (15 kg), resulting in the formation of a precipitate. The precipitated product was stirred for 1 h and then allowed to settle. The clear supernatant (~20 L) was removed from the top of the 50 L reactor system and purified water (~20 kg) was added. The resultant mixture was stirred for 10 min, filtered, washed with water (13 kg) and dried at 35-40° C. under vacuum to yield solid [5-(4,6-dimethyl-1H-benzoimidazol-2-yl)-4-methyl-pyrimidin-2-yl]-[3-(1-methyl-piperidin-4-yl)-propyl]-amine.

MS: [M H]$^+$=393

$^1$H NMR (600 MHz, Methanol-$d_6$) δpp, 1.38-1.43 (m, 2H), 1.43-1.52 (m, 2H), 1.53-1.61 (br, 1 H), 1.64-1.71 (m, 2H), 1.90-1.96 (br, m, 2H), 2.42 (s, 3H), 2.53 (s, 3H), 2.54 (s, 3H), 2.74 (s, 3H), 2.78-2.86 (br, m, 2H), 3.15-3.36 (m, 2H), 3.36-3.47 (m, 2H) 4.35 (s, 1H), 6.90 (s, 1H), 7.20 (s, 1H), 8.44 (br, s, 1H)

Step D: Preparation of Hemi-Tartrate of [5-(4,6-dimethyl-1H-benzoimidazol-2-yl)-4-methyl-pyrimidin-2-yl]-[3-(1-methyl-piperidin-4-yl)-propyl]-amine In a 100 L Hastelloy reactor, [5-(4,6-dimethyl-1H-benzoimidazol-2-yl)-4-methyl-pyrimidin-2-yl]-[3-(1-methyl-piperidin-4-yl)-propyl]-amine, prepared as in STEP C above (6.58 kg, 15.56 mol) was dissolved in denatured ethanol (31.00 kg, 955 ethanol/2-propanol) at about 48-52° C. After stirring for 15 minutes, the resultant hazy solution was cooled to about 25-30° C. Magnesium sulfate (0.60 kg) was added and the resultant mixture was stirred an additional 30 minutes. The magnesium sulfate was filtered over CELITE® (0.30 kg) and the resultant clear solution (KF=0.22%) was transferred to a clean glass lined 100 L glass-lined reactor and heated to about 48-52° C. A solution of L-tartaric add (1.16 kg, 7.73 mol) in denatured ethanol (10.0 kg) was charged to the reactor over 20 minutes. The resultant mixture was heated to about 70-75° C. and then aged for 1 h. The resultant yellow slurry was cooled to about 0-5'C over a 2 h period and then aged for 20 min. The product (as a precipitate) was filtered, washed with cold denatured ethanol (5.20 kg), then dried at about 75-80° C. under vacuum to yield the [5-(4,6-dimethyl-1H-benzoimidazol-2-yl)-4-methyl-pyrimidin-2-yl]-[3-(1-methyl-piperidin-4-yl)-propyl]-amine, as its corresponding hemi-tartrate solid salt.

Step E: Recrystallization

In a 100 L Hastelloy reactor, the hemi-tartrate of [5-(4,6-dimethyl-1H-benzoimidazol-2-yl)-4-methyl-pyrimidin-2-yl]-[3-(1-methyl-piperidin-4-yl)-propyl]-amine, prepared as in STEP D above (5.19 kg, 11.10 mol) was dissolved in a mixture of denatured ethanol (32.40 kg, 95/5 ethanol/2-propanol) and water (2.62 kg) at about 75-78° C. The resultant solution was cooled to about 50-55° C. and polish filtered (to remove any foreign particles) into a clean 100 L glass-lined reactor, followed by a rinse with denatured ethanol (4.15 kg). Denatured ethanol (25.62 kg) was added and the resultant solution was stirred and heated to about 78-80° C. to atmospherically distill off 51 L of the solvent. The resultant solution was cooled to about 55-60° C. and additional denatured ethanol (27,63 kg) was added, followed by heating to about 78-80° C. to atmospherically distill off 27 L of the solvent. The resultant solution was then cooled to about 50-55° C., seeded (2.0 g, 4.3 mmol), then further cooled to about 18-22° C. and then stirred for 1 h. The resultant precipitate was filtered, washed with denatured ethanol (5.00 kg) and dried at about 75-80° C. under vacuum to yield the solid hemi-tartrate of [5-(4,6-dimethyl-1H-benzoimidazol-2-yl)-4-methyl-pyrimidin-2-yl]-[3-(1-methyl-piperidin-4-yl)-propyl]-amine. m.p. 179° C.

The $^1$H NMR of a sample of the hemi-tartrate of [5-(4,6-dimethyl-1H-benzoimidazol-2-yl)-4-methyl-pyrimidin-2-yl]-[3-(1-methyl-piperidin-4-yl)-propyl]-amine was as follows: $^1$H NMR (300 MHz, Methanol-$d_4$) δ ppm 1.34-1.75 (m, o, 7 H), 1.88-1.99 (br, m, 2 H), 2.42 (s, 3 H), 2.53 (s, 3 H), 2.54 (s, 3 H), 2.75 (s, 3H), 2.76-2.89 (o, m, 2 H), 3.35-3.48 (m, 4 H), 4.35 (s, 1 H), 6.90 (s, 1 H), 7.20 (s, 1 H), 8.44 (br, s, 1 H)

EXAMPLE 2

[5-(4,6-Dimethyl-1H-benzoimidazol-2-yl)-4-methyl-pyrimidin-2-yl]-[3-(1-methyl-piperidin-4-yl)-propyl]-amine

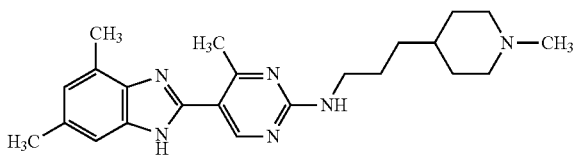

To a 4 mL vial were added 3,5-dimethyl-benzene-1,2-diamine.2HCl (69 mg, 0.33 mmol), 4-methyl-2-[3-(1-methyl-piperidin-4-yl)-propylamino]-pyrimidine-5-carbaldehyde (92 mg, 0.33 mmol), 2,3-dichloro-5,6-dicyano-p-benzoquinone (75 mg, 0.33 mmol), and DMF (2 mL). After addition of triethylamine (0.09 mL, 0.66 mmol), the resultant mixture was stirred for 5 hours at room temperature. The resultant mixture was then diluted with 1N NaOH (7.5 mL) and dichloromethane (7.5 mL). The organic layer was concentrated and purified by flash chromatography to yield the title compound.

MS: [M=H]$^+$=393

$^1$H NMR (600 MHz, Methanol-$d_6$) δ pp, 1.38-1.43 (m, 2H), 1.43-1.52 (m, 2H), 1.53-1.61 (br, 1H), 1.64-1.71 (m, 2H), 1.90-1.96 (br, m, 2H), 2.42 (s, 3H). 2.53 (s, 3H). 2.54 (s, 3H), 2.74 (s, 3H), 2.78-2.86 (br, m, 2H), 3.15-3.36 (m, 2H), 3.36-3.47 (m, 2H) 4.35 (s, 1H), 6.90 (s, 1H), 7.20 (s, 1H), 8.44 (br, s, 1H)

EXAMPLE 3

4-Methyl-2-[3-(1-methyl-piperidin-4-yl)-propylamino]-pyrimidine-5-carbaldehyde

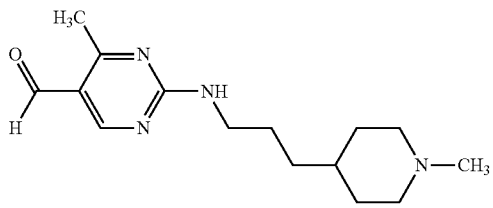 [SMILES: Cc1nc(NCCCC2CCN(C)CC2)ncc1C=O]

To a 5-L jacketed reactor equipped with overhead mechanical stirrer, nitrogen inlet, thermocouple probe, and J-Kem syringe pump was added 4-methyl-2-[3-(1-methyl-piperidin-4-yl)-propylamino]-pyrimidine-5-carbonitrile (160.0 g, 585 mmol) in THF (1.6 L). The resultant mixture was cooled to 5° C., and diisobutylaluminum hydride (DIBAL-H) (1 M in toluene, 1.755 L, 1.755 mol) was added by syringe pump over 2.33 hours, while maintaining an internal reaction temperature of <8° C. After completion of the addition, the resultant mixture was warmed to 20° C. over 40 min, then maintained an additional 3 hours at room temperature. The reaction was then quenched with aqueous $H_2SO_4$ (110 of sulfuric acid in water, 2 L total volume). The quench was executed over 1 hour with a jacket temperature of 0° C. and an internal temperature of 20-30° C. and was observed to be highly exothermic, (A Rochelle's salt quench was also explored. This approach was successful, but required long stirring times (after the quench) to yield two clear layers. An HCl quench was also employed and produced results similar to the sulfuric acid quench.) The resultant mixture was then stirred for 45 minutes and the aqueous layer and suspended solids were drained. The pH of the aqueous layer was adjusted to pH~10.6 with 50% NaOH (336 mL). Extraction of the aqueous layer (2×2 L dichloromethane) and concentration of the combined aqueous layers yielded an oil, which was used in the next step without further purification.

MS (electrospray): exact mass calculated for $C_{15}H_{23}N_5$, 276.20; m/z found, 277.1 [M+H]+.

EXAMPLE 4

[5-(4,6-Dimethyl-1H-benzoimidazol-2-yl)-4-methylpyrimidin-2-yl]-[3-(1-methyl-piperidin-4-yl)-propyl]-amine

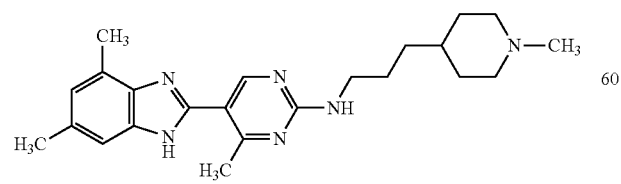

To a 2 L Erlenmeyer flask were added 3,5-dimethyl-benzene-1,2-diamine.2HCl (54.85 g, 262.3 mmol) and $Na_2S_2O_5$ (64.82 g, 341.0 mmol), as well as 4-methyl-2-[3-(1-methyl-piperidin-4-yl)-propylamino]-pyrimidine-5-carbaldehyde (prepared as in Example 3 above) (72.5 g, 262.3 mmol) in DMF (725 mL). After addition of triethylamine (73.1 mL, 524.6 mmol), the resultant mixture was warmed on a hot plate with stirring to 90° C. and held at this temperature for 2 hours. The resultant mixture was then concentrated to near dryness and partitioned between dichloromethane (0.7 L) and 1 N NaOH (1 L). The resultant mixture was stirred for 1 hour and then filtered to isolate the voluminous solid which had formed. The solids were dried and then partitioned between chloroform (700 mL) and saturated aqueous $NaHCO_3$ (700 mL). The layers were separated, the organic layer was dried over sodium sulfate and concentrated to a residue. The residue was recrystallized in hot heptane/ethyl acetate (1.8:1, 840 total volume) with initial hot filtration (~1 g of oily residues removed) and final filter cake washing with heptane/ethyl acetate (3:1, 250 mL total volume) to yield the title compound as a crystalline solid.

$^1$H-NMR: (400 MHz, $CD_3OD$) δ, 8.43 (s, 1H), 7,20 (s, 1H), 6,89 (s, 1H), 3,42 (t, J=7.0, 2H), 2,89-2.82 (m, 2H), 2.54 (s, 3H), 2.53 (s, 3H), 2.42 (s, 3H), 2.24 (s, 3H), 2.03-1.94 (m, 2H), 1.77-1.70 (m, 2H), 1,69-1.61 (m, 2H), 1.38-1.18 (m, 5H).

MS (electrospray): exact mass calculated for $C_{23}H_{32}N_6$, 392.27; m/z found, 393.2 [M+H]+.

Elemental Analysis for $C_{23}H_{32}N_6.0.25H_2O$: Calculated: C, 69,58; H, 8.25; N, 21.17; Measured: C, 69.45; H, 8.06; N, 21.30.

EXAMPLE 5

Hemi-tartrate of [5-(4,6-Dimethyl-1H-benzoimidazol-2-yl)-4-methyl-pyrimidin-2-yl]-[3-(1-methyl-piperidin-4-yl)-propyl]amine To a 50-mL reactor equipped with an overhead mechanical stirrer, liquid addition funnel, reflux condenser, internal temperature probe and dynamic nitrogen inlet were added [5-(4, 6-dimethyl-1H-benzoimidazol-2-yl)-4-methyl-pyrimidin-2-yl]-[3-(1-methyl-piperidin-4-yl)-propyl]-amine (1.01 g, 2.58 mmol) and EtOH (15 mL, 200 proof). The resultant heterogeneous solution was heated to 50° C., at which point the mixture was observed to become a homogeneous solution. At 50° C., a solution of L-tartaric acid (0.193 g, 1.29 mmol) dissolved in EtOH (5.0 mL, 200 proof) was added dropwise over 2.0 minutes. A slight precipitate was observed at the site of addition; however, the precipitate was not persistent. After completion of the addition, the resultant homogeneous solution was aged at 50° C. for 30 minutes. The resultant solution was then cooled to about 20° C. at which time nucleation was observed after ageing for ~30 min. The resultant slurry was aged at about 20° C. for 4.5 hours. The solids were collected by suction filtration and dried in a vacuum oven (under house vacuum) at 50° C. for 2.5 days. After complete solvent removal, the title compound was obtained as a crystalline solid.

EXAMPLE 6

Recrystallization of Hemi-tartrate of [5-(4,6-Dimethyl-1H-benzoimidazol-2-yl)-4-methyl-pyrimidin-2-yl]-[3-(1-methyl-piperidin-4-yl)-propyl]-amine A representative sample of the hemi-tartrate of compound of formula (I-A), prepared as described in Example 5 above, was recrystallized as follows. To a 500-mL, round bottom flask equipped with an overhead mechanical stirrer, reflux condenser and internal temperature probe were added the hemi-tartrate of [5-(4,6-dimethyl-1H-benzoimidazol-2-yl)-4-methyl-pyrimidin-2-yl]-[3-(1-methyl-piperidin-4-yl)-propyl]-amine (8.03 g, 17.2 mmol) and EtOH (160 mL, 200 proof). The resultant heterogeneous mixture was warmed to reflux (77.3° C.). At reflux, H$_2$O was added dropwise via syringe (1.6 mL) and a homogeneous solution was achieved. The resultant solution was aged at reflux for 30 minutes then cooled to about 21.3° C. over a 90-minute period. Once this temperature was reached, nucleation was observed after ~30 min. The resultant slurry was aged at this temperature for an additional 4 hours. The solids were collected by suction filtration and dried at room temperature under house vacuum for 20 hours. The cake was further dried at 50° C. in a vacuum oven for 20 hours to yield the title compound as a crystalline solid.

EXAMPLE 8

[5-(5-Fluoro-4-methyl-1H-benzoimidazol-2-yl)-4-methyl-pyrimidin-2-yl]-[3-(1-methyl-piperidin-4-yl)-propyl]-amine

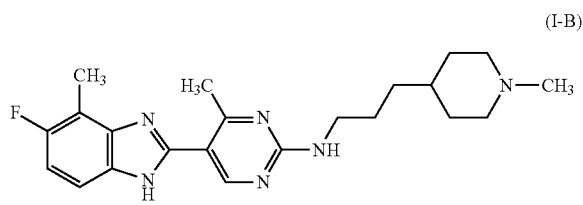

(I-B)

To a 2 L Erlenmeyer flask were added 4-fluoro-3-methyl-benzene-1,2-diamine.HCl (46.32 g, 262.3 mmol), Na$_2$S$_2$O$_5$ (64.82 g, 341.0 mmol), and 4-methyl-2-[3-(1-methyl-piperidin-4-yl)-propylamino]-pyrimidine-5-carbaldehyde (72.5 g, 262.3 mmol) in DMF (725 L). To the resultant mixture was then added triethylamine (36.6 mL, 262.3 mmol), and the reaction was warmed on a hot plate with stirring to 90° C. and held at this temperature for 2 hours. The resultant mixture was then concentrated to near dryness and partitioned between dichloromethane (1 L) and 1 N NaOH (1 L). After separation of the layers, the aqueous layer was extracted a second time with dichloromethane (1 L). The combined organic layers were then washed with saturated aqueous NaHCO$_3$ (1.6 L). The organics were then extracted with a 1 M mono/dibasic phosphate buffer (pH 5.62, 1.23 L. The aqueous layer was then basified with 50% NaOH (80 mL) to pH 10.8. The resultant heterogeneous layer was then extracted with dichloromethane (1.5 L and 500 mL), and the combined organics were concentrated to yield the title compound.

The title compound was recrystallized from hot heptane/ethyl acetate (2:1, 1.15 L total volume) with initial hot filtration and final filter cake washing with heptane/ethyl acetate (3:1, 250 mL total volume) to yield the title compound as a crystalline solid.

$^1$H-NMR: (400 MHz, CD$_3$OD) δ, 8.45 (s, 1H), 7.37 (dd, J=8.8, 4,4 Hz, 1H), 6.99 (dd, J=10.3, 8.8 1H), 3.42 (t, J=7.0, 2H), 2.89-2.82 (m, 2H), 2.54 (s, 3H), 2.49 (d, J=1.6 Hz, 3H), 2.24 (s, 3H), 2.03-1.94 (m, 2H), 1.77-1.70 (m, 2H), 1.69-1.61 (m, 2H), 1.38-1.18 (m, 5H).

MS (electrospray): exact mass calculated for C$_{22}$H$_{29}$FN$_6$, 396.2; m/z found, 397.2 [M+H]$^+$ Elemental Analysis for C$_{22}$H$_{29}$FN$_6$: Calculated: C, 66.64; H, 7.37; N, 21.19. Measured: C, 66.31; H, 7.61; N, 21.19.

EXAMPLE 9

[5-(4,6-Dimethyl-1H-benzoimidazol-2-yl)-4-methyl-pyrimidin-2-yl]-[3-(1-methyl-piperidin-4-yl)-propyl]-amine

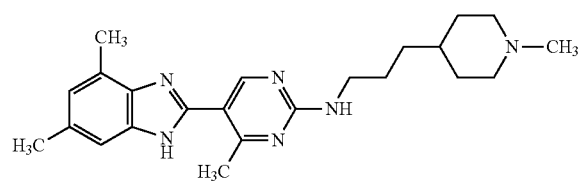

Step A 4-methyl-2-[3-(1-methyl-piperidin-4-yl)-propylamino]-pyrimidine-5-carbonitrile (10.0 g, 36.6 mmol) was slurried in dry toluene (80.7 g) under a nitrogen atmosphere. At 3-10° C. diisobutylaluminum hydride (DIBAL-H) (20% in toluene) (62.6 g, 88.0 mmol) was added over 80 min. The resulting mixture was kept at 10-20° C. for 65 min, then ethyl acetate (9.0 g, 102.1 mmol) was added over 15 min. After stirring for 30 min at room temperature, the resulting yellow solution was added dropwise to a solution of 37% aqueous hydrochloric acid (16.0 g, 162.4 mmol) in water (70.0 g) over 60 min at about 20° C. (exothermic reaction, gas formation). The resulting biphasic mixture was stirred at room temperature over night, then sodium hydroxide (30% in water) (34.1 g, 255.8 mmol) was added over 20 min, resulting in the formation of a third layer (orange oil). The mixture was stirred at 35-40° C. for 30 min, then the layers were allowed to separate and the aqueous layer and the orange middle layer were removed. The toluene layer was then extracted with a mixture of 37% aqueous hydrochloric add (3.60 g, 36.5 mmol) and water (60.4 g) at room temperature. The aqueous layer (containing 4-methyl-2-[3-(1-methyl-piperidin-4-yl)-propylamino]-pyrimidine-5-carbaldehyde) was used in the next step without further purification or product isolation.

Step B

In a clean reactor, sodium metabisulfite (4.87 g, 25.6 mmol) and 3,5-dimethyl-benzene-1,2-diamine.1.5HCl (4.87 g, 25.6 mmol) were slurried in water (64.9 g). 37% Aqueous hydrochloric acid (3.61 g, 36.5 mmol) was added. To the resulting mixture was then added the aqueous layer solution prepare din STEP A above, over 9 min at room temperature (slightly exothermic). The resulting mixture was then heated to 55-65° C. and maintained at this temperature for 2-3 hours (open reactor, O$_2$ from air). Upon completion of the reaction (as determined by HPLC), the resulting mixture was cooled to room temperature and filtered to remove any insoluble salts that had precipitated.

Step C

Potassium carbonate (25.3 g, 183.0 mmol) was dissolved in water (100.0 g) at room temperature, 2-methyltetrahydrofurane (9.0 g) was added, and then the filtrate as prepared in STEP B was added dropwise over 60 min, resulting in precipitation of the desired product. The resulting suspension was stirred overnight at room temperature, the precipitate was isolated by filtration and washed with water (60.5 g), to yield the title compound as a yellow solid.

EXAMPLE 10

[5-(4,6-Dimethyl-1H-benzoimidazol-2-yl)-4-methyl-pyrimidin-2-yl]-[3(1-methyl-piperidin-4-yl)-propyl]-amine

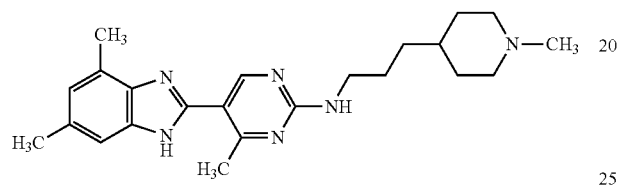

Step A 4-methyl-2-[3-(1-methyl-piperidin-4-y)-propylamino]-pyrimidine-5-carbaldehyde (prepared from 4-methyl-2-[3-(1-methyl-piperidin-4-yl)-propylamino]-pyrimidine-5-carbonitrile by reduction with Raney-Nickel) (20.0 g, 72.4 mmol) was suspended in water (60.0 g) at room temperature. Hydrochloric acid (37% in water) was added dropwise until the solid had completely dissolved (10.0 g, 101.5 mmol).

Step B

A 1 L-reactor was then charged with sodium sulfite (9.15 g, 72.6 mmol) and 3,5-dimethyl-benzene-1,2-diamine.2HCl (15.2 g, 72.7 mmol). The solids were slurried in water (120.0 g) at room temperature and hydrochloric acid (37% in water, 4.25 g, 43.1 mmol) was added, followed by the addition of water (20.0 g). The resulting mixture was stirred for approx, 5 min, then heated to 45-50° C. The solution prepared in STEP A was added in 2 portions over 40 min, and the resulting mixture stirred (open reactor, O₂ from air) for 2 h 20 min at 55-62° C. The resulting mixture was then cooled to 45° C. and sodium hydroxide (30% in water) (11.5 g, 86.3 mmol) followed by 2-methyltetrahydrofurane (200.0 g) were added. After the pH was adjusted with sodium hydroxide (30% in water) (27.3 g, 204.8 mmol), the resulting biphasic mixture was stirred at 45-52° C. for 25 min. The resulting phases were separated and the aqueous layer was removed. To the organic layer was added water (100.0 g) and the resulting mixture stirred at 45-52° C. for 20 min. The resulting phases were again allowed to separate and the aqueous layer was removed. To the organic layer was added dropwise, cyclohexane (122.0 g) over approx. 60 min at 50° C. After the addition was complete, the resulting mixture was slowly cooled to room temperature, during which time crystallization set in spontaneously. The resulting mixture was maintained at 0° C. for 2 h, the solid was isolated by filtration, washed with cyclohexane (61.0 g) and dried in vacuo at 65° C. to yield the title compound as a light yellow solid.

EXAMPLE 11

[5-(4,6-Dimethyl-1H-benzoimidazol-2-yl)-4-methyl-pyrimidin-2-yl]-[3-(1-methyl-piperidin-4-yl)-propyl]-amine

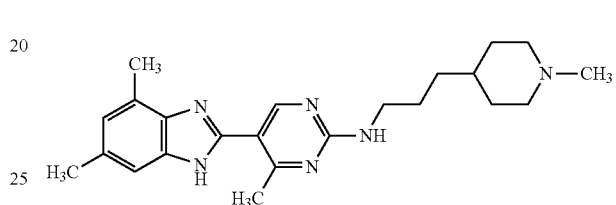

Step A 4-methyl-2-[3-(1-methyl-piperidin-4-yl)-propylamino]-pyrimidine-5-carbaldehyde (prepared from 4-methyl-2-[3-(1-methyl-piperidin-4-yl)-propylamino]-pyrimidine-5-carbonitrile by reduction with Raney-Nickel) (22.5 g, 81.4 mmol) was suspended in water (67.7 g) at room temperature. Hydrochloric acid (37% in water) (9.67 g, 98.1 mmol) was added dropwise until the solid had completely dissolved.

Step B

A 500 mL-reactor was charged with sodium sulfite (10.30 g, 81.8 mmol) and 3,5-dimethyl-benzene-1,2-diamine.2HCl (17.10 g, 81.7 mmol). The solids were slurried in water (135.6 g) at room temperature and hydrochloric acid (37% in water) (6.40 g, 64.9 mmol) in water (21.6 g) was added. The mixture resulting was heated to 45-50° C. in 20 min. To the resulting mixture was then added dropwise, over 30 mins the solution prepared in STEP A. The resulting mixture was then heated to 60° C. for 2.5 h (open reactor, O₂ from air). Upon completion of the reaction (as monitoring by HPLC), the resulting mixture was filtered to remove any insoluble salts that had precipitated.

Step C

In a clean 500 mL-reactor, potassium carbonate (56.27 g, 407.2 mmol) was dissolved in water (202.5 g), and then 2-methyltetrahydrofurane (20.3 g) was added at room temperature. The filtrate prepared as in STEP B above was then added dropwise over 2 h. The resulting yellowish suspension was stirred over night at room temperature, and the resulting precipitate isolated by filtration and washed with water.

The reactor was then charged with the wet product/precipitate (49.26 g) and 2-methyltetrahydrofurane (200.0 g), and the resulting mixture heated to 50° C. to dissolve the solid. The resulting solution was washed twice with a mixture sodium hydroxide (30% in water) (7.58 g, 60.6 mmol and 7.56, 60.8 mmol, respectively) in water (40.0 g, 40.5 g, respectively) at 45-55° C. and once with water (40.1 g). After removal of the aqueous layer, cyclohexane (135.0 g) was added dropwise over 50 min at 50° C., during which time, crystallization was observed to set in spontaneously. The resulting mixture was then slowly cooled, then maintained at 0° C. for 1 h. The precipitate was isolated by filtration, washed with cyclohexane (60.0 g) and dried in vacuo at 65° C. to yield the title compound as a light yellow solid.

EXAMPLE 12

Hemi-tartrate of [5-(4,6-Dimethyl-1H-benzoimidazol-2-yl)-4-methyl-pyrimidin-2-yl]-[3-(1-methyl-piperidin-4-yl)-propyl]-amine A 2 L-reactor was charged with [5-(4,6-Dimethyl-1H-benzoimidazol-2-yl)-4-methyl-pyrimidin-2-yl]-[3-(1-methyl-piperidin-4-yl)-propyl]-amine (200.0 g, 486 mmol) in a nitrogen atmosphere. Denatured ethanol (770.0 g) followed by isopropanol (230 g) were added and the resulting mixture was heated to 45° C. to yield a clear, yellow solution. To this solution was added a solution of L-(+) tartaric acid (36.5 g, 243 mmol) in denatured ethanol (294.0 g) at 40-50° C. over 70 min. The resulting solution was maintained at 40-50° C. for 75 min, over which time crystallization was observed to occur. The resulting suspension was slowly cooled to 15° C., maintained at this temperature overnight, then cooled further to 0° C. After 3 h 15 min at 0° C., the title compound as a precipitate was isolated by filtration, washed with cold denatured ethanol (400 g) and dried in vacuo at 45° C. to yield the title compound as a slightly yellow, crystalline solid.

EXAMPLE 13

Hemi-tartrate of [5-(4,6-Dimethyl-1H-benzoimidazol-2-yl)-4-methyl-pyrimidin-2-yl]-[3-(1-methyl-piperidin-4-yl)-propyl]-amine

[5-(4,6-Dimethyl-1H-benzoimidazol-2-yl)-4-methyl-pyrimidin-2-yl]-[3-(1-methyl-piperidin-4-yl)-propyl]-amine (4.6 g, 10.8 mmol) was dissolved in denatured ethanol (24.3 g) at 40-50° C. Cyclohexane (15.6 g) was added and the resulting mixture was heated to reflux at atmospheric pressure to distill off solvent. The azeotropic distillation was continued until the reflux temperature reached 75° C. After distillation, denatured ethanol (12.5 g) was added and the resulting solution was stirred at 40-50° C. A solution of L-(+) tartaric acid (0.80 g, 5.4 mmol) in denatured ethanol (6.7 g) was added over 45 min, and the resulting mixture maintained at 40-50° C. for 40 min, then seeding crystals of the desired hemi-tartrate. The resulting thin suspension was maintained at 40-50° C. for 4 h, then slowly cooled to room temperature and maintained at room temperature overnight. The resulting mixture was then cooled to 0° C. for 30-60 min, the resulting precipitate isolated by filtration, washed with denatured ethanol (10.0 g) in 2 portions and dried in vacuo at 40-50° C. to yield the title compound as a white crystalline solid.

EXAMPLE 14

Recrystallization of Hemi-tartrate of [5-(4,6-Dimethyl-1H-benzoimidazol-2-yl)-4-methyl-pyrimidin-2-yl]-[3(1-(1-methyl-piperidin-4-yl)-propyl]-amine A 500 mL-reactor was charged with [5-(4,6-dimethyl-1H-benzoimidazol-2-yl)-4-methyl-pyrimidin-2-yl]-[3-(1-methyl-piperidin-4-yl)-propyl]-amine hemi-tartrate (24.0 g, 25.7 mmol) and methanol (63.0 g). The resulting mixture was warmed to 50° C. for 15 min, until all the solids were observed to dissolve. Denatured ethanol (105.0 g) was then added and the resulting solution was filtered (at 50° C.) to remove any remaining particles. The filtrate was heated briefly to reflux, then cooled to approx. 60° C., before seeding with crystals of the desired hemi-tartrate. The resulting mixture was subjected to the following temperature profile for crystallization: 1 h at 60° C., cooling to 40° C. over 2 h, heating to 50° C. over 1 h, cooling to 30° C. over 2 h, heating to 40° C. over 1 h, cooling to 20° C. over 2 h, heating to 30° C. over 1 h, cooling to 10° C. over 2 h, heating to 20° C. over 1 h, then cooling to 0° C. over 2 h. The resulting suspension was maintained at 0° C. for 7 h, then the resulting solid precipitate was isolated by suction filtration, washed with denatured ethanol (3×30.0 g) and dried in vacuo at 40° C. to yield the title compound as a white crystalline solid.

EXAMPLE 15

4-Methyl-2-[3-(1-methyl-piperidin-4-yl)-propylamino]-pyrimidine-5-carbaldehyde

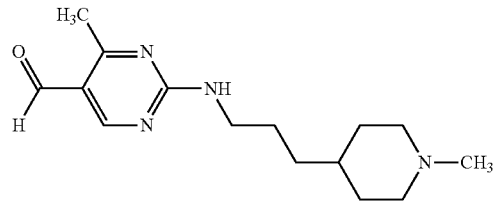

The following procedure represents a recipe for the preparation of the title compound. The title compound was prepared several times following the recipe detailed below.

A vessel at room temperature was charged with formic acid (800 mL) and 4-methyl-2-(3-(1-methylpiperidin-4-yl)propylamino)pyrimidine-5-carbonitrile (100 g) and the resulting mixture stirred to yield a clear solution, then cooled to 10-15° C. Water (200 mL) was added and the resulting mixture cooled to −2 to 0° C. To the resulting mixture was then added RANEY® nickel (160 g) maintaining the temperature at −2 to 0° C. and then stirred at this temperature for 2-3 hours. The resulting mixture was then filtered to remove the RANEY® nickel and the filtercake washed with water (100 mL). The filtrate was cooled to 0-5° C. and then slowly treated with 50% sodium carbonate solution in water (3.0 L) to adjust the pH of the solution to pH~10. Toluene (400 mL) was added and the resulting mixture stirred at room temperature for about 30 minutes, then allowed to settle for about 1 hour. The resulting layers were separated and the aqueous layer washed with toluene (400 mL×2). The combined toluene layer and washed were distilled at 55-60° C. to remove the toluene, to yield the title compound as an oily residue.

To the residue was added hexane (100 mL), the resulting mixture stirred for 30 minutes, then distilled under vacuum to yield a residue. To this residue was added hexane (200 mL) and the resulting mixture cooled to 10-15° C., then stirred at this temperature for 1 hour, resulting in the formation of a precipitate. The resulting mixture was filtered and the filter-cake washed with hexane (50 mL) and then dried first under vacuum and then in an air oven at 30-35° C. to yield the title compound as a white to light yellow solid.

EXAMPLE 16

Oral Formulation

As a specific embodiment of an oral composition, 100 mg of the compound prepared as in Example 1 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A crystalline hemi-tartrate of compound of formula (I-A)

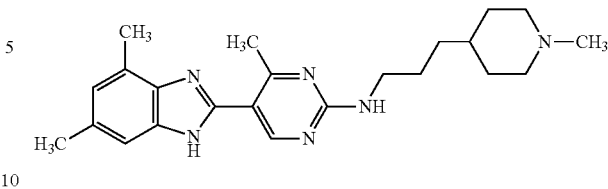

whose powder X-ray diffraction spectrum comprises the following powder X-ray diffraction peaks:

| Pos. [°2θ] | d-spacing [Å] |
|---|---|
| 6.49 | 13.62 |
| 8.58 | 10.30 |
| 10.35 | 8.55 |
| 10.75 | 8.23 |
| 23.60 | 3.77. |

* * * * *